United States Patent
Shannon

(10) Patent No.: US 9,950,038 B2
(45) Date of Patent: Apr. 24, 2018

(54) METHODS AND COMPOSITIONS FOR INHIBITING DELAYED GRAFT FUNCTION

(75) Inventor: Richard P. Shannon, Philadelphia, PA (US)

(73) Assignee: THE TRUSTEES OF THE UNIVERSIY OF PENNSYLVANIA, Philadelphia, PA (US)

( * ) Notice: Subject to any disclaimer, the term of this patent is extended or adjusted under 35 U.S.C. 154(b) by 191 days.

(21) Appl. No.: 14/235,627

(22) PCT Filed: Feb. 8, 2012

(86) PCT No.: PCT/US2012/049295
§ 371 (c)(1),
(2), (4) Date: May 19, 2014

(87) PCT Pub. No.: WO2013/022692
PCT Pub. Date: Feb. 14, 2013

(65) Prior Publication Data
US 2014/0309169 A1 Oct. 16, 2014

Related U.S. Application Data

(60) Provisional application No. 61/515,390, filed on Aug. 5, 2011, provisional application No. 61/534,438, filed on Sep. 14, 2011.

(51) Int. Cl.
| | | |
|---|---|---|
| *A61K 38/00* | (2006.01) | |
| *A01N 63/00* | (2006.01) | |
| *A01N 65/00* | (2009.01) | |
| *A61K 38/26* | (2006.01) | |
| *A01N 1/02* | (2006.01) | |

(52) U.S. Cl.
CPC ............ *A61K 38/26* (2013.01); *A01N 1/0226* (2013.01)

(58) Field of Classification Search
None
See application file for complete search history.

(56) References Cited

U.S. PATENT DOCUMENTS

| | | |
|---|---|---|
| 2002/0055460 A1 | 5/2002 | Coolidge et al. |
| 2003/0031657 A1 | 2/2003 | Habener et al. |
| 2004/0097411 A1 | 5/2004 | Shannon et al. |
| 2011/0048980 A1 | 3/2011 | Seman |
| 2012/0040892 A9 | 2/2012 | Zimmer et al. |

FOREIGN PATENT DOCUMENTS

WO WO 2007/046834 4/2007

OTHER PUBLICATIONS

Kur et al., "Clinical Heart Transplantation With Extended Preservation Time (>5 Hours): Experience With University of Wisconsin Solution," Transpl. Proc. 41:2247-2249 (2009).*
Bose et al., "Glucagon like peptide-1 is protective against myocardial ischemia/reperfusion injury when given either as a preconditioning mimetic or at reperfusion in an isolated rat heart model," Cardiovasc. Drugs Thera. 19:9-11 (2005).*
Robertson, "Islet Transplantation as a Treatment for Diabetes—A Work in Progress," N. Eng. J. Med. 350:694-705 (2004).*
Urusova et al., "GLP-1 inhibition of pancreatic islet cell apoptosis," Trends Endo. Meta.15:27-33 (2004).*
Akhtar et al., Novel Approaches to Preventing Ischemia-Reperfusion Injury During Liver Transplantation, Transplant. Proc. 45:2083-2092 (2013).*
Sonne et al., "Protective effects of GLP-1 analogues exendin-4 and GLP-1(9-36) amide against ischemia—reperfusion injury in rat heart," Reg. Pept. 146:243-249 (2008).*
Ban et al., "Cardioprotective and Vasodilatory Actions of Glucagon-Like Peptide 1 Receptor Are Mediated Through Both Glucagon-Like Peptide 1 Receptor-Dependent and -Independent Pathways," Circul. 117: 2340-2350 (2008).*
Bhashyam et al., 2010, "Glucagon-Like Peptide-1 Increases Myocardial Glucose Uptake via p38a MAP Kinase-Mediated, Nitric Oxide-Dependent Mechanisms in Conscious Dogs With Dilated Cardiomyopathy," Circ Heart Fail 3:512-521.
DeLeon et al., "Glucagon-like peptide-1 response to acarbose in elderly type 2 diabetic subjects," Diabetes Res. Clin. Pract., May 2002; 56 (2):101-6.
Drucker D J, "Biological actions and therapeutic potential of the glucagons-like peptides," Gastroenterology, 2002; 122:531-44.
Fields et al., "Glucagon-like Peptide-1 and Myocardial Protection: More than Glycemic Control," Clin. Cardiol., 2009, 32(5):236-243.
Halbirk et al., 2010, "Cardiovascular and metabolic effects of 48-h glucagon-like peptide-1 infusion in compensated chronic patients with heart failure Am" J Physiol Heart Circ Physiol. 298:H1096-1102.
Hupe-Sodmann et al., "Characterisation of the processing by human neutral endopeptidase 24.11 of GLP-1(7-36) amide and comparison of the substrate specificity of the enzyme for other glucagon-like peptides." Regul Pept (Aug. 22, 1995) vol. 58, No. 3, pp. 149-156.
Meneilly et al., "Glucagon-Like Peptide-1 (7-37) Augments Insulin Mediated Glucose Uptake in Elderly Patients with Diabetes," J. Gerentol. Med. Sci., 2001:56A, M681-5.
Mauvais-Jarvis et al., "Therapeutic perspectives for type 2 diabetes mellitus: molecular and clinical insights," Diabetes Metab., Sep. 2001; 27 (4 Pt 1):415-23.
Meneilly et al., "Effect of Glucagon-Like Peptide-1 on Non-Insulin Mediated Glucose Uptake in the Elderly Patient with Diabetes," Diabetes Care, 2001; 24:1951 56.
Nikolaidis et al., 2004, "Recombinant Glucagon-Like Peptide-1 Increases Myocardial Glucose Uptake and Improves Left Ventricular Performance in Conscious Dogs With Pacing-Induced Dilated Cardiomyopathy," Circulation 110:955-961.
Sokos et al., "Glucagon-Like Peptide-1 Infusion Improves Left Ventricular Ejection Fraction and Functional Status in Patients With Chronic Heart Failure," Journal of Cardiac Failure, 2006, 12(9):694-699.
Bose et al., 2005, "Glucagon-like peptide 1 can directly protect the heart against ischemia/reperfusion injury," Diabetes, 45:146-51.
Nikolaidis et al., 2004, "Effects of glucagon-like peptide-1 in patients with acute myocardial infarction and left ventricular dysfunction after successful reperfusion," Circulation 109:962-5.
Zhao et al., 2006, "Direct effects of glucagon-like peptide-1 on myocardial contractility and glucose uptake in normal and postischemic isolated rat hearts," J Pharmacol Exp Ther 317:1106-13.

* cited by examiner

*Primary Examiner* — Julie Ha
*Assistant Examiner* — Kristina M Hellman
(74) *Attorney, Agent, or Firm* — Riverside Law LLP

(57) ABSTRACT

Disclosed are compositions and methods for inhibiting preventing, reducing delayed graft function, allograft rejection or ischemia reperfusion injury.

19 Claims, 14 Drawing Sheets

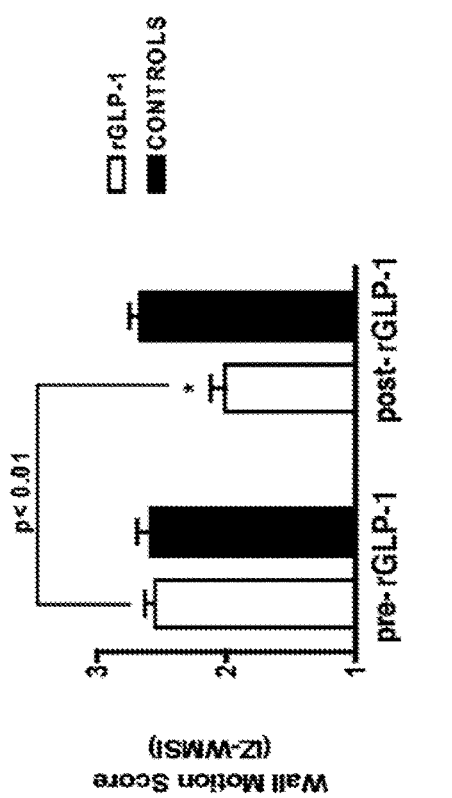
Figure 1A
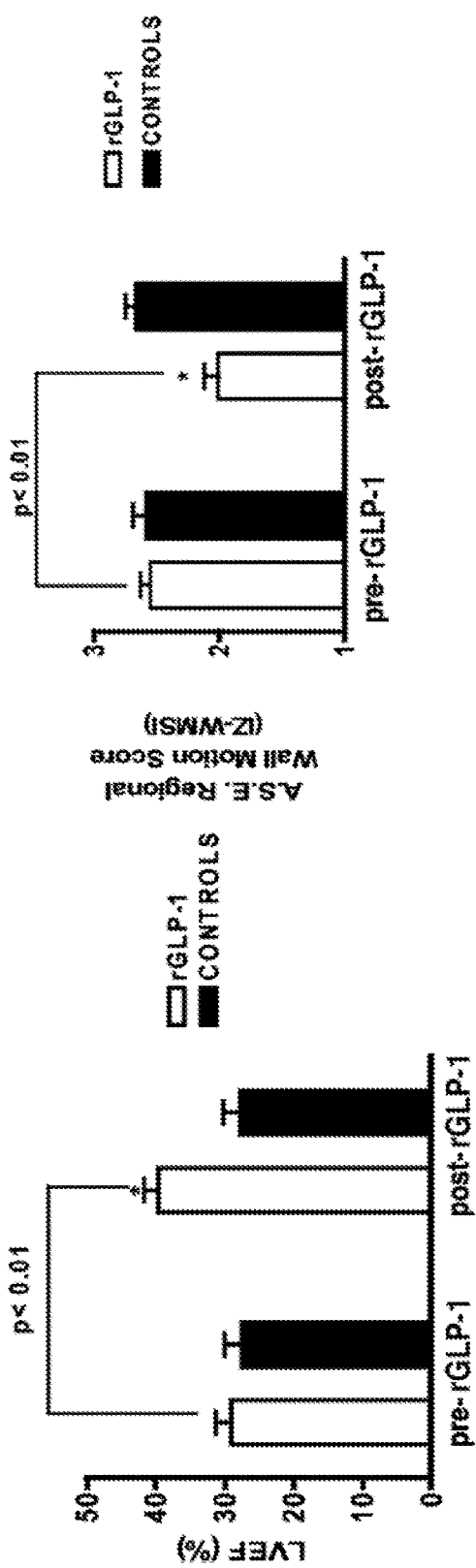
Figure 1B
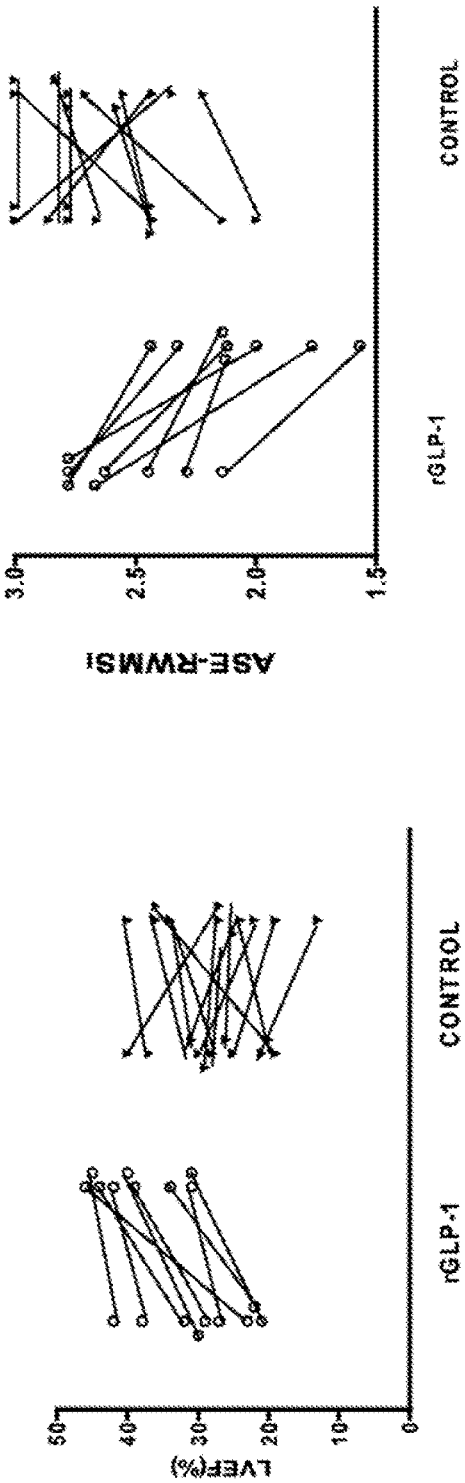

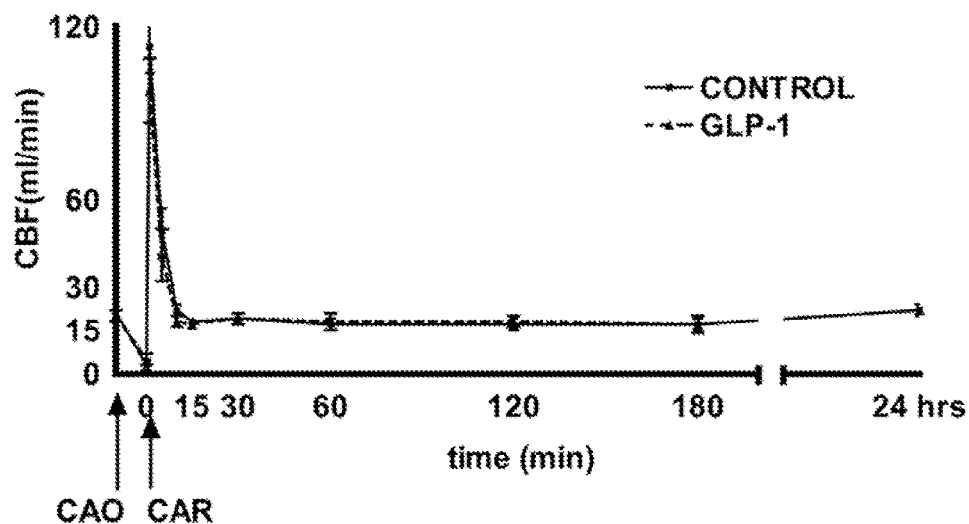
Figure 2A  CORONARY BLOOD FLOW RESPONSE
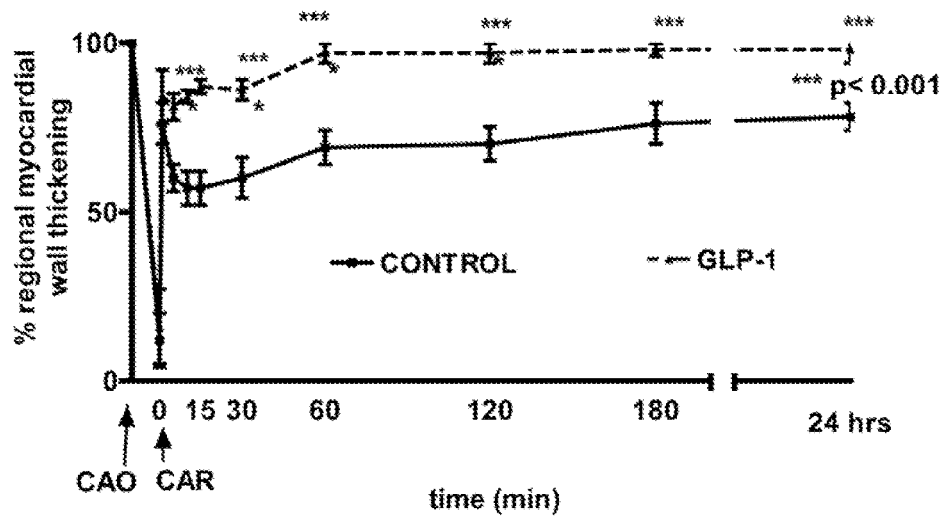
Figure 2B  REGIONAL POST-ISCHEMIC CONTRACTILE FUNCTION
*** $p < 0.001$ versus control by ANOVA Chronic Conscious Pig Model With Bi-Ventricular Failure With Impaired Renal Blood Flow Impaired renal blood flow but not cardiac output in pigs with biventricular failure Impaired renal blood flow but not cardiac output in pigs with biventricular failure Favorable effects of GLP-1 on renal blood flow and Glomerular Filtration Rate Table 3. Effect of GLP-1 on Renal and Metabolic Function

| | Control (n = 9) | |
|---|---|---|
| | Baseline | 5 weeks |
| BNP (pg/mL) | 296 ± 128 | 285 ± 152 |
| HbA1C (%) | 6.6 ± 0.6 | 6.7 ± 0.6 |
| [Na+] (mmol/L) | 141 ± 1 | 140 ± 1 |
| BUN (mg/dL) | 16 ± 2 | 23 ± 7 |
| Cr (mg/dL) | 1.0 ± 0.1 | 1.1 ± 0.1 |

| | GLP-1 (n = 12) | |
|---|---|---|
| | Baseline | 5 weeks |
| BNP (pg/mL) | 289 ± 90 | 218 ± 102 |
| HbA1C (%) | 7.7 ± 0.4 | 6.9 ± 0.4 |
| [Na+] (mmol/L) | 140 ± 1 | 141 ± 1 |
| BUN (mg/dL) | 27 ± 6 | 27 ± 3 |
| Cr (mg/dL) | 1.3 ± 0.1 | 1.4 ± 0.2 |

BNP, B-type natriuretic peptide; BUN, blood urea nitrogen; Cr, creatinine; GLP-1, glucagon-like peptide-1.

GLP-1 induces a natriuresis in patients with heart failure requiring a reduction in diuretic use

FIG. 6

Proposed GLP-1 Signaling Pathway in Normal Myocardium

METHODS AND COMPOSITIONS FOR INHIBITING DELAYED GRAFT FUNCTION

CROSS-REFERENCE TO RELATED APPLICATIONS

This application is the U.S. national phase application filed under 35 U.S.C. § 371 claiming benefit to International Patent Application No. PCT/US2012/049295, filed on Aug. 2, 2012, which is entitled to priority under 35 U.S.C. § 119(e) to U.S. Provisional Patent Application No. 61/515,390, filed Aug. 5, 2011 and U.S. Provisional Patent Application No. 61/534,438, filed Sep. 14, 2011, each of which application are hereby incorporated herein by reference in their entirety.

BACKGROUND

The universal organ donor shortage has greatly mitigated the benefits associated with organ transplantation and has led to expanding criteria for donors and lengthening lists for transplantation. A contributing factor to this resource shortage is the graft dysfunction that is observed in a high percentage of organ transplantation.

Delayed graft function (DGF) is a well-known complication affecting the kidney, heart, lung and liver allografts in the immediate post-transplantation period. The frequency of DGF ranges from 5 to 50% in deceased-donor kidney transplants. DGF is usually the result of predominant ischemic injury to the graft before and during procurement and is further aggravated by the reperfusion injury, a multi-factorial event in which immunologic factors also playa role. Indeed, ischemia and immune injury may playa synergistic pathological role in the syndrome. DGF generally leads to a more complex post-operative course for the patient. In addition, DGF is associated with prolonged hospitalization, higher transplantation costs and adverse effects on the rehabilitation of transplant recipients. The deleterious effects of DGF in the immediate post-transplant period are well known. If the ischemia reperfusion injury in DGF leads to incomplete recovery due to inability of the allograft cells to regenerate completely, then the functioning graft will have reduced survival due to reduced cellular mass. Furthermore, allo-immune responses that are known to be accentuated during DGF can contribute either to acute rejection or to accelerated cellular atrophy, reducing graft survival. On the other hand, if DGF is completely reversible, then there should be no effect of DGF on longer term graft survival. Recent evidence suggests that patients with DGF are at a 41% increased risk of graft loss at 3 years. Recent studies have attempted to use corticosteroids to prevent DGF but these interventions have not proven to be efficacious. What is needed are new methods and compositions for the prevention, inhibition, or reduction of DGF.

SUMMARY

Disclosed are methods and compositions related to inhibiting and/or preventing delayed graft function.

The methods of the present invention are used in a continuous infusion of donor and recipient subjects.

The methods also relate to administration to a recipient subject wherein there is an acute allograft rejection.

BRIEF DESCRIPTION OF THE DRAWINGS

The accompanying drawings, which are incorporated in and constitute a part of this specification, illustrate several embodiments and together with the description illustrate the disclosed compositions and methods.

FIG. 1 shows that GLP-1 improves functional recovery following myocardial ischemia. CBF and respective regional wall thickening responses to CAO and CAR. The CBF response (top) is characterized by reactive hyperemia followed by gradual return of flow to pre-occlusion levels in both control and GLP-1-treated animals. The different patterns of recovery of regional contractile function between the two groups are illustrated (bottom).

FIG. 2, comprising FIG. 2A and 2B, show that GLP-1 improves myocardial functional recovery following acute myocardial infarction in humans. FIG. 2A shows changes in LVEF after 72 hours of rGLP-1 infusion versus control subjects. Lower panel illustrates individual data. FIG. 2B shows changes in regional wall motion score at the peri-infarct zone in rGLP-1-treated patients versus control subjects. Lower panel illustrates individual data.

FIG. 6 shows that GLP-1 induces a natriuresis in patients with heart failure requiring a reduction in diuretic use.

DETAILED DESCRIPTION

Figure 3:
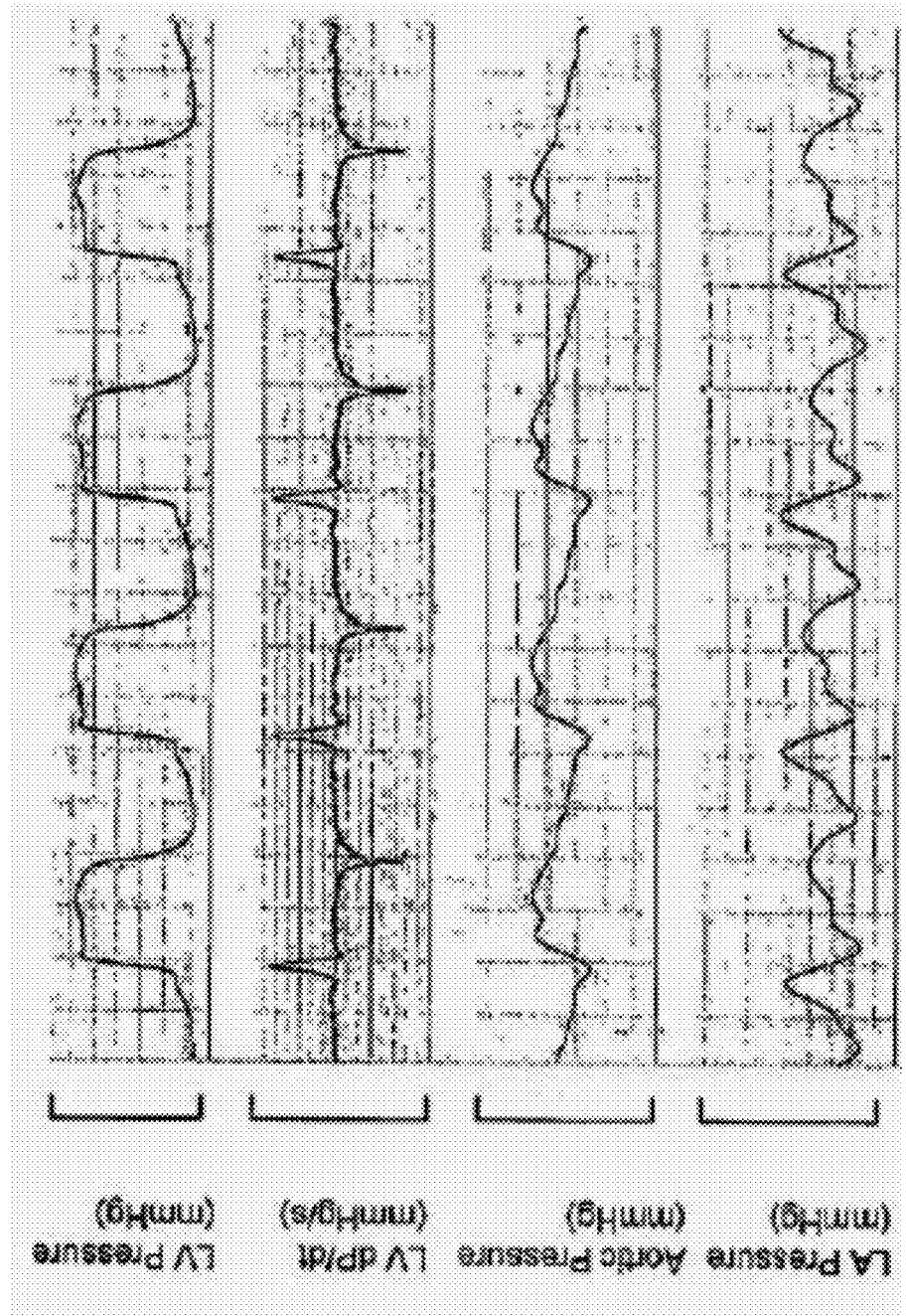
FIG. 3 shows the Chronic Conscious Pig Model with Bi-Ventricular Failure with Impaired Renal Blood Flow.
Figure 3:
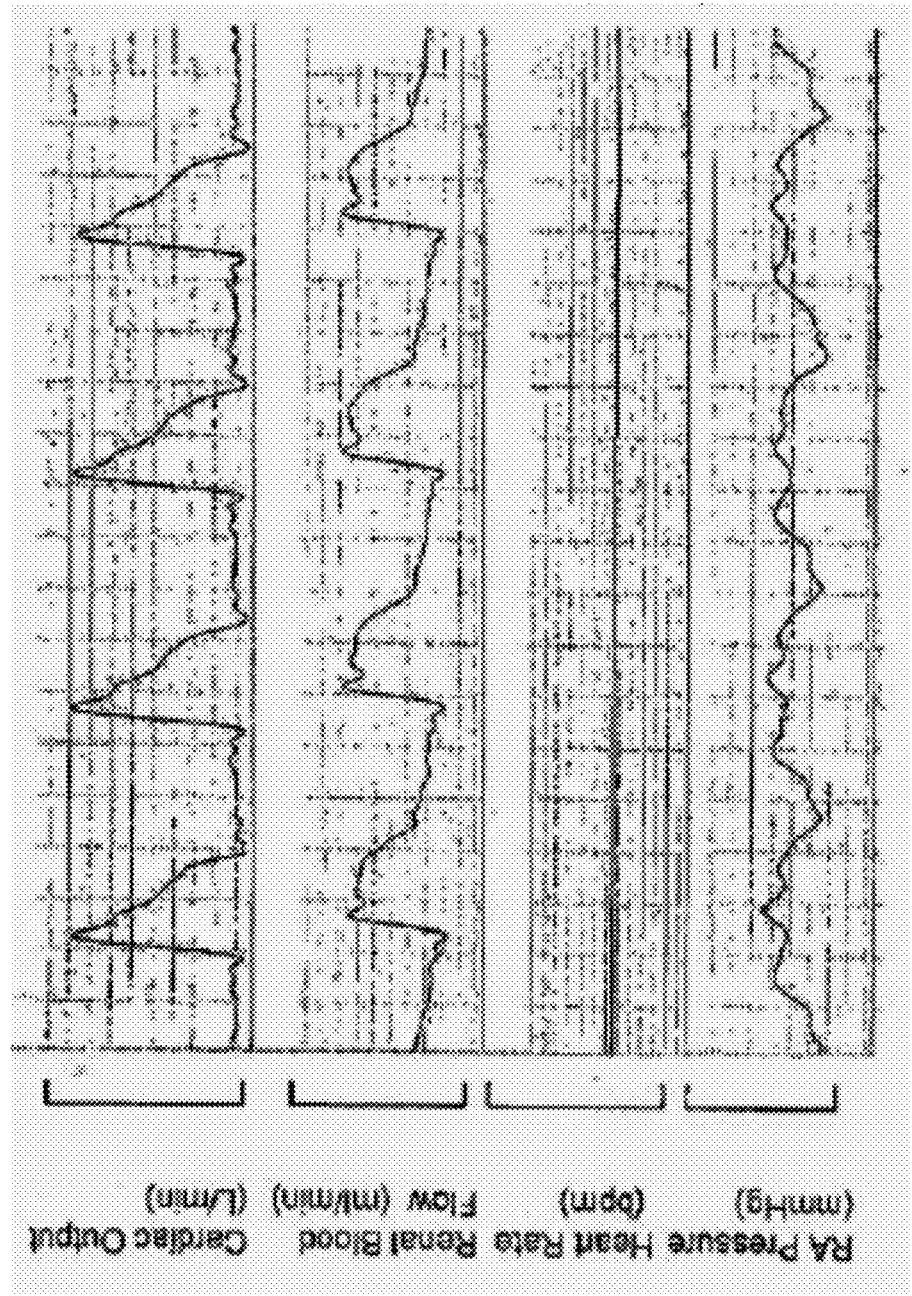
Figure 3:
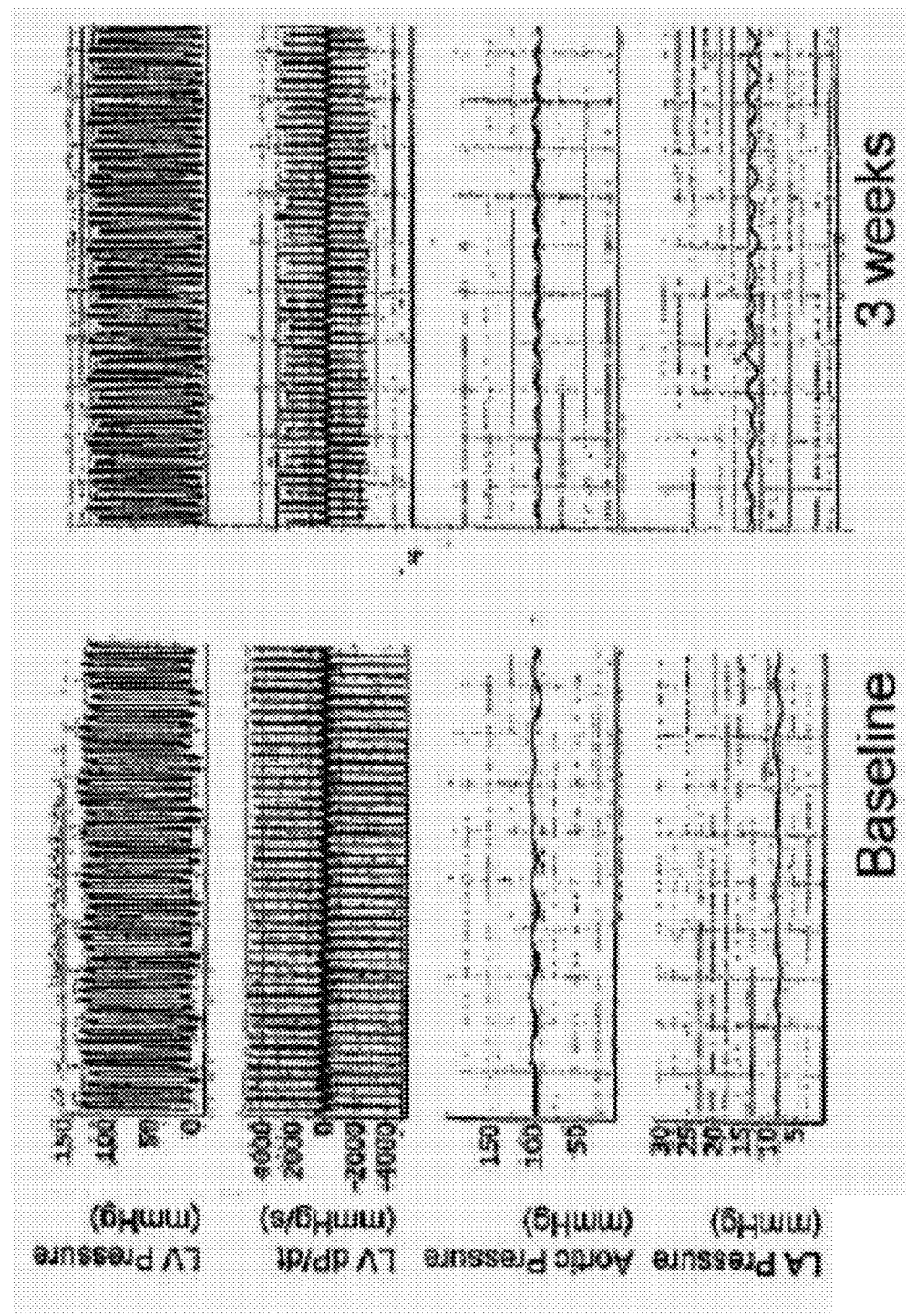
Figure 3:
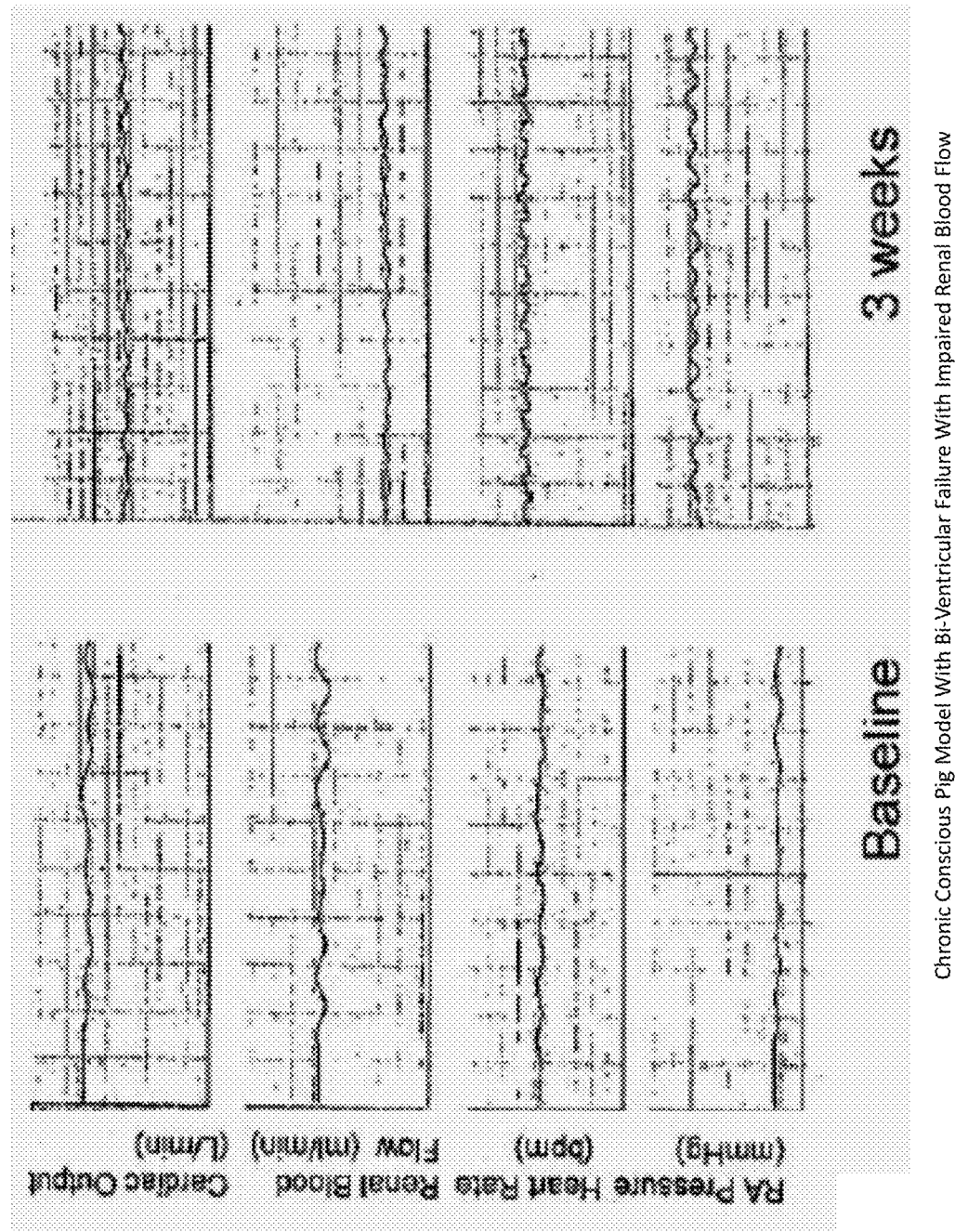

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

The disclosed methods are designed to prevent, inhibit, or reduce DGF. As used herein, "inhibition," "inhibit," or "inhibiting" mean to decrease an activity, response, condition, disease, or other biological parameter. This can include but is not limited to the complete ablation or prevention of the activity, response, condition, or disease. This may also include, for example, a 10% reduction in the activity, response, condition, or disease as compared to the native or control level. Thus, the reduction can be at least a 10% reduction as compared to native or control levels. Additionally, a reduction can refer to at least a 20% reduction as compared to native or control levels. Also, a reduction can refer to at least a 30% reduction as compared to native or control levels. Moreover, a reduction can refer to at least a 40% reduction as compared to native or control levels Also, a reduction can refer to at least a 50% reduction as compared to native or control levels. Additionally, a reduction can refer to at least a 60% reduction as compared to native or control levels. In another aspect, a reduction can refer to at least a 70% reduction as compared to native or control levels. In addition, a reduction can refer to at least an 80% reduction as compared to native or control levels. Also, a reduction can refer to at least a 90% reduction as compared to native or control levels. Lastly, a reduction can refer to a 100% reduction as compared to native or control levels. Thus, as disclosed herein to inhibit allograft failure means to reduce the occurrence, reduce the effects, or delay the onset of the events the result in allograft failure relative to an untreated control.

"Reducing," "reduce," or "reduction" in the context of a delayed graft function, allograft rejection, ischemia reperfusion injury, or disease or condition described herein refers to a decrease in the cause, symptoms, or effects of a disease or condition. It is understood that the reduction of a disease or condition can be any statistically significant reduction in the cause, symptoms, or effects of a disease or condition including, but not limited to, a reduction in the disease or condition itself. Therefore, in the disclosed methods, "reducing" can refer to at least a 10%, decrease in the amount of a disease or condition such as delayed graft function, ischemic reperfusion injury, or allograft rejection (including but not limited to acute or chronic rejection). Additionally, "reducing" can refer to at least a 20%, decrease in the amount of a disease or condition such as delayed graft function, ischemic reperfusion injury, or allograft rejection. Also, "reducing" can refer to at least a 30%, decrease in the amount of a disease or condition such as delayed graft function, ischemic reperfusion injury, or allograft rejection. "Reducing" can also refer to at least a 40%, decrease in the amount of a disease or condition such as delayed graft function, ischemic reperfusion injury, or allograft rejection. Furthermore, "reducing" can refer to at least a 50%, decrease in the amount of a disease or condition such as delayed graft function, ischemic reperfusion injury, or allograft rejection. Moreover, "reducing" can refer to at least a 60%, decrease in the amount of a disease or condition such as delayed graft function, ischemic reperfusion injury, or allograft rejection. It is also contemplated that "reducing" can refer to at least a 70%, decrease in the amount of a disease or condition such as delayed graft function, ischemic reperfusion injury, or allograft rejection. Additionally, "reducing" can refer to at least an 80%, decrease in the amount of a disease or condition such as delayed graft function, ischemic reperfusion injury, or allograft rejection. Also "reducing" can refer to at least a 90% or 100% decrease in the amount of a disease or condition such as delayed graft function, ischemic reperfusion injury, or allograft rejection.

Methods of Using the Compositions

Disclosed herein are methods of preventing, reducing, or inhibiting delayed graft function (DGF). Delayed graft function is a syndrome associated with acute graft dysfunction following transplantation. DGF is associated with increased allograft immunogenicity and risk of acute rejection episodes, and decreased long-term survival. The compositions and methods disclosed herein are designed to reduce, inhibit, or prevent DGF thereby increasing the long term survival of the allograft and/or preventing allograft rejection. This is particularly advantageous for pediatric allograft recipients as the typical graft survival time is 6 years and the recipient will need use of the allograft for their entire life.

Ischemic/Reperfusion Injury

It is understood that DGF involves characteristics of immunological insults and ischemic/reperfusion injury. It is further understood that there are many known causes of ischemia/reperfusion injury. For example, an ischemic/reperfusion injury can result from ischemia reperfusion event such as myocardial ischemia, myocardial reperfusion, subendocardial ischemia, Takayasu's arteritis, including but not limited to (ischemic strokes (including strokes resulting from cerebral thrombosis, cerebral embolism, and atrial fibrillation), hemorrhagic strokes (including strokes resulting from aneurysm and arteriovenous malformation), and transient ischemic attack), pulmonary infarction, hypoxia, retinal ischemia, renal ischemia, cardiac surgery where a heart lung machine is used such as Coronary artery bypassing, preservation of organs for transplant, and mechanical injuries such as amputation.

Stroke

A stroke, also known as cerebrovascular accident (CVA), is an acute neurological injury in which the blood supply to a part of the brain is interrupted. That is, a stroke involves the sudden loss of neuronal function due to disturbance in cerebral perfusion. This disturbance in perfusion is commonly arterial, but can be venous. The part of the brain with disturbed perfusion no longer receives adequate oxygen. This initiates the ischemic cascade which causes brain cells to die or be seriously damaged, impairing local brain function. Risk factors include advanced age, hypertension (high blood pressure), diabetes mellitus, high cholesterol, and cigarette smoking.

Strokes can be classified into two major categories: ischemic and hemorrhagic. Ischemia can be due to thrombosis, embolism, or systemic hypoperfusion. Hemorrhage can be due to intracerebral hemorrhage or subarachnoid hemorrhage. ~80% of strokes are due to ischemia. In an ischemic stroke, which is the cause of approximately 85-90% of strokes, a blood vessel becomes occluded and the blood supply to part of the brain is totally or partially blocked. Ischemic stroke is commonly divided into thrombotic stroke, embolic stroke, systemic hypoperfusion (Watershed or Border Zone stroke), or venous thrombosis.

Spinal Cord Compression

Spinal cord compression develops when the spinal cord is compressed by a tumor, abscess or other lesion, or by physical trauma. It is regarded as a medical emergency independent of its cause, and requires swift diagnosis and treatment to prevent long-term disability due to irreversible spinal cord injury.

Renal Ischemia

Renal ischemia, also called nephric ischemia, is the deficiency of blood in one or both kidneys, or nephrons, usually due to functional constriction or actual obstruction of a blood vessel. Ischemia/reperfusion (I/R) injury of the kidney is a common cause of acute renal failure (ARF) and is associated with high morbidity and mortality in the intensive care unit.

Cardiac Ischemia

Cardiac ischemia is a situation in which the flow of oxygen-rich blood to the heart muscle is impeded, resulting in inadequate oxygenation of the heart. The most common cause of cardiac ischemia is plaque buildup in the arteries due to the long-term effects of coronary artery disease. This plaque buildup narrows the arteries to the point where the amount of blood flowing through the arteries is not enough to supply oxygen-rich blood to the heart, especially during times of physical exertion or emotional stress.

The lack of oxygen is often temporary, and symptoms can include a type of chest pain, pressure or discomfort called angina. These episodes may last anywhere between 2 and 20 minutes. However, many episodes of ischemia do not have any associated symptoms (silent ischemia).

Lengthy episodes of cardiac ischemia can be a sign of a heart attack. A heart attack occurs when a blood clot blocks the flow of blood to the heart muscle. It can occur in an artery already narrowed by plaque (atherosclerosis), or a heart attack can occur after a blood clot breaks off from its original site and travels through the arteries. The blockage causes a sudden and possibly complete interruption of oxygen-rich blood flow, and the resulting heart attack could cause permanent damage and scarring to the portion of the heart muscle supplied by the blocked artery.

Allograft Survival

It is understood and herein contemplated that one way in which DGF or ischemia and reperfusion injury can occur is through tissue or organ grafting. When harvesting the donor tissue or organ blood flow is cut off from the donor tissue or organ creating ischemia. When the donor tissue or organ has been implanted and blood flow from the recipient to the donor tissue or organ restored reperfusion injury can occur. This early ischemia/reperfusion injury can greatly affect allograft survival. In fact, for a kidney graft, nephron can be irreversibly lost due to this ischemic/reperfusion injury. Moreover, the ischemic injury combined with the added inflammatory and immunological responses to the graft result in DGF further increasing risk of graft loss. Therefore, in one aspect, disclosed herein are methods of inhibiting allograft rejection and therefore increasing graft survival in a graft recipient comprising contacting (e.g., infusing or perfusing) a donor organ, tissue, or cell with a composition comprising GLP-1 peptide (28-36) or GLP-1 metabolite (9-36) amide and administering to recipient of the graft a composition comprising a therapeutically effective amount of GLP-1 peptide (28-36), GLP-1 (7-36)amide, or GLP-1 metabolite (9-36)amide or an analogue or derivative thereof. It is understood and herein contemplated that the disclosed methods of preventing or inhibiting allograft rejection applies to both acute and chronic rejections. In the disclosed methods, the subject can be a transplant recipient and the injured tissue/organ the donor graft. For example, the organ/tissue graft can be a renal graft such as a kidney, cornea, lung, heart, liver, skin, and bone marrow). Thus, it is contemplated herein that the disclosed methods contemplate administering the disclosed GLP-1 peptide compositions to both the recipient and the donor or donor organ or tissue.

Because of the aspects of DGF associated with immunological responses and ischemia/reperfusion injury, the methods disclosed herein are not limited to DGF. Therefore, disclosed herein are methods of preventing, reducing, or inhibiting allograft rejection, injury due to stroke, or ischemic/reperfusion injury.

Glucagon-Like Peptide-1

In one aspect, the disclosed methods of preventing, reducing, or inhibiting DGF, injury due to stroke, ischemic/reperfusion injury, or allograft rejection comprise treating the donor organ and the recipient with a peptide derived from Glucagon-like peptide-1 (GLP-1). GLP-1, an insulinotropic hormone, is secreted postprandially by intestinal L cells as a proteolytic cleavage product of pre-pro-glucagon. It is know as an incretin or gut hormone. GLP-1 has pleiotropic biological effects and the clinical implications of which are very important for type II diabetic patients. GLP-1 has been shown to be a transcriptional inducer of islet cell-specific genes. It stimulates insulin secretion by beta cells in response to an increase in glucose levels and is also responsible for inhibition of glucagon secretion and a decrease in the rate of gastric emptying and acid secretion. GLP-1 has been shown to increase islet cell mass by promoting beta cell neogenesis from ductal cells. The role of GLP-1 in glucose tolerance and the possible involvement of this peptide hormone in the pathogenesis of diabetes make it a candidate as a new therapeutic agent for people with Type II diabetes. However, its potential as a new therapeutic agent is limited because this peptide cannot be administered orally, and it has a short half life (about 5 minutes or less) in vivo.

GLP-1 is a product of post-translational processing of the glucagon precursor proglucagon in intestinal L cells and the brain. Other peptide hormones derived from proglucagon include glucagon (in the pancreas) and oxyntomodulin and GLP-2 (in the intestines and brain). GLP-1 stimulated insulin release is carefully controlled in an autocrine fashion, minimizing the risks of hypoglycemia that are associated with exogenous insulin administration. In addition, GLP-1 and its analogues have insulin-independent actions, including the inhibition of gastric emptying, reduction of food ingestion, beta islet cell hypertrophy, and, importantly, the inhibition of glucagon.

There are two forms of full length N-terminal GLP-1, GLP-1 (1-37) and GLP-1 (1-36)amide (HAEGTFTSDVS-SYLEGQAAKEFIAWLVKGR SEQ ID NO: 1). Both forms are active and are produced when the GLP-1 polypeptide is cleaved to remove the first six amino acids resulting in the active peptides GLP-1 (7-37), having 31 amino acids, and GLP-1 (7-36) amide, having 30 amino acids. The majority of circulating biologically active GLP-1 is found in the amidated form, GLP-1 (7-36) amide, with lesser amounts of the bioactive non-amidated GLP-1 (7-37) also detectable. The active GLP-1 undergoes rapid degradation by N-terminal cleavage of the first two amino acids ($His^1$-$Ala^2$) to a 9-36 peptide (EGTFTSDVSSYLEGQAAKEFIAWLVKGR SEQ ID NO: 2) by circulating di-peptidyl peptidase IV (DPPIV) which exists in blood and tissues resulting in an active half-life time of GLP-1 of 1-2 minutes. Additionally, GLP-1 is easily excreted from the kidney, so its half-life time in blood is within 5 min. Accordingly, most pharmaceutical companies are focusing on the development of long acting analogues of GLP-1 that are DPPIV resistant to treat Type II diabetes. While such long acting agents may be effective in stimulating pancreatic insulin release, the manipulations utilized to make GLP-1 analogues long acting result in reduced efficacy ischemic preconditioning of the allograft.

It is understood and herein contemplated that there are unique benefits associated with the use of the native peptide, GLP-1 (7-36) amide and that these benefits are attributable to the active metabolites, GLP-1 (9-36) amide and GLP-1 (28-36) (FIAWLVKGR SEQ ID NO: 3). Therefore, disclosed herein are methods of preventing, reducing, or inhibiting DGF, allograft rejection (including but not limited to acute and chronic allograft rejection), or ischemic/reperfusion injury, comprising administering a composition comprising GLP-1 peptide (28-36), GLP-1 (7-36)amide, and/or GLP-1 metabolite (9-36) amide. Also disclosed are methods of preventing, reducing, or inhibiting DGF, allograft rejection (including but not limited to acute rejection, chronic rejection, or delayed rejections), or ischemic/reperfusion injury, comprising contacting a donor organ, tissue, or cell with a composition comprising GLP-1 peptide (28-36), GLP-1 (7-36)amide, and/or GLP-1 metabolite (9-36) amide; and administering to graft recipient the composition comprising GLP-1 peptide (28-36), GLP-1 (7-36)amide, and/or GLP-1 metabolite (9-36) amide. It is understood that the graft and the recipient can receive the same or different compositions. Accordingly, disclosed herein are methods of preventing, reducing, or inhibiting DGF, allograft rejection, or ischemic/reperfusion injury, comprising contacting a donor organ, tissue, or cell with a first composition comprising GLP-1 peptide (28-36), GLP-1 (7-36)amide, and/or GLP-1 metabolite (9-36) amide; and administering to a graft recipient a second composition comprising GLP-1 peptide (28-36), GLP-1 (7-36)amide, and/or GLP-1 metabolite (9-36) amide. It is further understood that there are instances where long-term administration of a composition comprising GLP-1 is desirable to prolong graft survival and that the GLP-1 composition utilized long-term can be the same or different that the composition administered to the recipient at the time of engraftment. Accordingly also contemplated herein are methods further comprising administering to the recipient a third composition comprising GLP-1 peptide (28-36), GLP-1 (7-36)amide, and/or GLP-1 metabolite (9-36) amide.

Wherein the medical procedure does not involve the transplant of tissues, organs, or cells such as during injury due to stroke or ischemic/reperfusion injury not associated with allograft, it is understood that the disclosed methods comprise the administration of GLP-1 peptide (28-36), GLP-1 (7-36)amide, or GLP-1 metabolite (9-36)amide to a subject. Thus, disclosed herein are methods of preventing, reducing, or inhibiting ischemic/reperfusion injury or injury due to stroke in a subject comprising administering to the subject a composition comprising GLP-1 peptide (28-36), GLP-1 (7-36)amide, and/or GLP-1 metabolite (9-36)amide.

It is further contemplated that the GLP-1 compositions described herein are useful to prevent, reduce, inhibit, or treat graft rejection (including but not limited to acute and chronic rejection) including instances where the graft was not transplanted using the methods disclosed herein. Accordingly, the GLP-1 treatment to prevent, reduce, inhibit, graft rejection in a graft recipient can be administered weeks, months, or years following engraftment to prevent graft rejection and insure graft survival. It is understood that methods to prevent, reduce, or inhibit graft rejection can involve a single discreet administration of the GLP-1 compositions described herein, multiple administrations of the GLP-1 compositions, or continuous administration of the GLP-1 compositions.

Because the methods herein reduce, inhibit, or prevent a condition such as DGF, allograft rejection (including, for example, acute rejection), ischemia reperfusion injury, or injury due to stroke, it is understood that by "treatment" and "treating" is meant the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, ameliorization, stabilization or prevention. It is understood and herein contemplated that "treatment" does not necessarily refer to a cure of the disease or condition or a complete prevention of infarct, but can involve, for example, an improvement in the outlook of an ischemia/reperfusion injury. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount. It is further understood that in the case of allograft rejection, DGF, and ischemic reperfusion injury treatment can refer to prophylactic measures to intend to ameliorate the conditions causing allograft rejection, DGF, and ischemic reperfusion injury or to reduce the effects of or prevent allograft rejection, DGF, and ischemic reperfusion injury. It is further understood that the disclosed methods and compositions can be used to treat both acute and chronic conditions such as acute rejection or a chonic allograft rejection.

In one aspect of the disclosed methods, a GLP-1 peptide (28-36), GLP-1 (7-36)amide, or GLP-1 metabolite (9-36) amide composition is administered once at preconditioning of the graft or following injury due to stroke or ischemic/reperfusion injury. In another aspect, a more continuous administration of the composition occurs. For example, it is contemplated herein that the disclosed methods utilize multiple discreet administrations of a GLP-1 peptide (28-36), GLP-1 (7-36)amide, or GLP-1 metabolite (9-36) amide composition or a continuous administration through infusion or use of recombinant vectors. It is further understood that the disclosed methods utilize multiple routes of administration at various times during a treatment procedures such as discreet perfusion or bathing ex vivo of a donor organ, tissue, or cell in combination with continuous infusion of the recipient subject. Alternatively, a subject with an injury from a stroke or ischemic/reperfusion injury may receive an initial injection of a GLP-1 composition at one dose and continuous infusion at the same or different dose during a stabilization period.

It is also disclosed herein that combinations of GLP-1 peptide (28-36), GLP-1 (7-36)amide, or GLP-1 metabolite (9-36)amide can be administered throughout the treatment regimen. Thus, it is contemplated that the composition administered to the donor or donor graft are different from the preconditioning regimen which in turn can be different from the composition used for maintenance. For example, a donor graft can be contacted with a composition consisting of GLP-1 (7-36)amide and a pharmaceutical carrier while the recipient of the graft is preconditioned with a GLP-1 (9-36)amide composition, and long term maintenance is conducted through the administration of GLP-1 (28-36) to the recipient. Therefore, specifically contemplated is each and every combination of the GLP-1 compositions disclosed herein for use in the methods of preventing, reducing, or inhibiting DGF, allograft rejection (including but not limited to acute and chronic rejection), injury due to stroke, or ischemic/reperfusion injury described herein. For example, it is specifically contemplated that the entire method of preventing, reducing, or inhibiting DGF, allograft rejection, injury due to stroke, or ischemic/reperfusion injury can be accomplished by administering a composition consisting of GLP-1 peptide (28-36), GLP-1 (7-36)amide, or GLP-1 metabolite (9-36)amide and a pharmaceutical carrier one time to the graft prior to harvest. Also disclosed herein are method of preventing, reducing, or inhibiting DGF, allograft rejection, injury due to stroke, or ischemic/reperfusion injury wherein a composition consisting of GLP-1 peptide (28-36), GLP-1 (7-36)amide, or GLP-1 metabolite (9-36) amide is administered at discreet time points such as prior to graft harvest, preconditioning the recipient, at time of transplant, and for at least 72 hours thereafter. It is further contemplated that additional discreet doses could be used to maintain the graft or reduce, prevent, or inhibit graft rejection. Also disclosed are methods of preventing, reducing, or inhibiting DGF, allograft rejection, injury due to stroke, or ischemic/reperfusion injury wherein a first composition comprising GLP-1 peptide (28-36), GLP-1 (7-36)amide, or GLP-1 metabolite (9-36)amide is used to contact the graft and a different second composition comprising GLP-1 peptide (28-36), GLP-1 (7-36)amide, or GLP-1 metabolite (9-36)amide is used to administer to the recipient. It is further contemplated that a still different third composition are administered at a time point after the second composition is administered.

Further examples of combinations of GLP-1 compositions include but are not limited to a first composition comprising GLP-1 (28-36), the second composition comprising GLP-1 (9-36)amide, and where used a third composition comprising GLP-1 (7-36)amide; a first composition comprising GLP-1 (28-36), the second composition comprising GLP-1 (7-36)amide, and where used a third composition comprising GLP-1 (9-36)amide; a first composition comprising GLP-1 (9-36) amide, the second composition comprising GLP-1 (7-36)amide, and where used a third composition comprising GLP-1 (28-36); a first composition comprising GLP-1 (9-36)amide, the second composition comprising GLP-1 (28-36), and where used a third composition comprising GLP-1 (7-36)amide; a first composition comprising GLP-1 (7-36)amide, the second composition comprising GLP-1 (9-36)amide, and where used a third composition comprising GLP-1 (28-36); a first composition comprising GLP-1 (7-36)amide, the second composition comprising GLP-1 (28-36), and where used a third composition comprising GLP-1 (9-36)amide; the first and second composition comprising GLP-1 (28-36) and the third composition comprises GLP-1 (9-36)amide or GLP-1 (7-36) amide; the first and third composition comprising GLP-1 (28-36) and the second composition comprises GLP-1 (9-36)amide or GLP-1 (7-36)amide; the first and second composition comprising GLP-1 (7-36)amide and the third composition comprises GLP-1 (9-36)amide or GLP-1 (28-36); the first and third composition comprising GLP-1 (7-36)amide and the second composition comprises GLP-1 (9-36)amide or GLP-1 (28-36); the first and second composition comprising GLP-1 (9-36)amide and the third composition comprises GLP-1 (7-36)amide or GLP-1 (28-36); the first and third composition comprising GLP-1 (9-36)amide and the second composition comprises GLP-1 (7-36)amide or GLP-1 (28-36); the first composition comprising GLP-1 (7-36)amide and the second and third composition comprises GLP-1 (9-36)amide or GLP-1 (28-36); the first composition comprising GLP-1 (9-36)amide and the second and third composition comprises GLP-1 (9-36)amide or GLP-1 (28-36); and the first composition comprising GLP-1 (28-36) and the second and third composition comprises GLP-1 (9-36)amide or GLP-1 (7-36)amide.

The disclosed GLP-1 peptide (28-36), GLP-1 (7-36) amide, or GLP-1 metabolite (9-36) amide compositions is administered at several time points during a treatment regimen. Thus, for example disclosed herein are methods of preventing, reducing, or inhibiting DGF, allograft rejection, or ischemic/reperfusion injury, comprising contacting a donor organ, tissue, or cell with a first composition comprising GLP-1 peptide (28-36), GLP-1 (7-36)amide, and/or GLP-1 metabolite (9-36) amide; and administering to graft recipient a second composition comprising GLP-1 peptide (28-36), GLP-1 (7-36)amide, and/or GLP-1 metabolite (9-36) amide, wherein the recipient receives continuous infusion from 24 hours prior the time of harvest to at least 72 hours after harvest. Also disclosed are methods wherein the recipient receives continuous infusion form the time of harvest to at least 72 hours after harvest. It is further disclosed that in cases where long term survival of a graft or long-term maintenance is needed, periodic discreet injections, continuous infusion, or recombinant delivery techniques (such as the use of a viral vector comprising a nucleic acid which encodes for GLP-1 peptide (28-36), GLP-1 (7-36)amide, and/or GLP-1 metabolite (9-36) amide) are used.

It is understood and herein contemplated that the disclosed methods of preventing, reducing, or inhibiting DGF, allograft rejection, or ischemic/reperfusion injury utilize organs, tissues, or cells from live or cadaveric donors. It is further understood that the donor organs are kidney, liver, lung, heart, skin, cornea and bone marrow. Where the donor is a live donor, contact of the GLP-1 composition with the donor graft occurs through any of the routes of administration discussed herein including but not limited to parenteral routes such as continuous infusion and intravenous injection. Where the donor is a cadaveric donor ex vivo methods of contacting the GLP-1 composition and the donor graft are used including but not limited to perfusion and bathing of the graft. It is also contemplated herein that where ex vivo methods are employed to contact the graft with a GLP-1 composition, the composition further comprises a cryopreservative such as Wisconsin solution.

One advantage of the disclosed methods is that a single infusion in the donor can precondition all target organs simultaneously as well as condition the recipient regardless of the organ being engrafted. A further advantage is where the donor tissue, cell, or organ receives a separate infusion relative to the graft recipient; the infusion can utilize the same pharmaceutical formulation. Nevertheless, it is also understood and contemplated herein that the disclosed methods utilize different pharmaceutical compositions between the donor or donor organ and the recipient. It is also contemplated that the composition administered to the recipient change at different stages of the procedure. For example, the composition can be different during one or more of preconditioning, grafting, the first 72 hours, or during long term maintenance (e.g., when necessary to prevent long term graft rejection).

Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered parenterally such as for example, intravenously, intramuscular injection, intraperitoneal injection, subcutaneous injection, transdermal injection, or continuous infusion such as an intravenous drip device. It is further understood that when the referring to situations involving a cadaveric graft, administration can be through direct perfusion of the donor tissue or organ. The exact amount of the compositions required will vary from subject to subject, depending on the species, age, weight and general condition of the subject, the severity of the allergic disorder being treated, the particular nucleic acid or vector used, its mode of administration and the like. An appropriate amount can be determined by one of ordinary skill in the art using only routine experimentation given the teachings herein for the various compositions of the present invention.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129:57-80, (1992); and Roffler, et al., *Biochem. Pharmacol*, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis have been reviewed (Brown and Greene, *DNA and Cell Biology* 10:6, 399-409 (1991)).

Pharmaceutically Acceptable Carriers

It is disclosed herein that the disclosed GLP-1 (7-36) amide, GLP-1 (9-36)amid, or GLP-1 (28-36) peptide or analogs or derivatives thereof can be used therapeutically in combination with a pharmaceutically acceptable carrier. Thus, disclosed herein are methods of preventing, reducing, or inhibiting delayed graft function, allograft rejection, stroke, or ischemia reperfusion injury comprising contacting a donor organ, tissue, or cell with a first composition comprising GLP-1 peptide (28-36), GLP-1 (7-36)amide, or GLP-1 metabolite (9-36) amide and a pharmaceutically acceptable carrier; and administering to graft recipient a second composition comprising GLP-1 peptide (28-36,) GLP-1 (7-36)amide, or GLP-1 metabolite (9-36) amide and a pharmaceutically acceptable carrier. It is understood and herein contemplated that in some instances formulations comprising more than the pharmaceutically acceptable carrier and a GLP-1 peptide may not be desirable. Therefore, also disclosed are methods of preventing, reducing, or inhibiting delayed graft function, allograft rejection, stroke, or ischemia reperfusion injury comprising contacting a donor organ, tissue, or cell with a first composition consisting of GLP-1 peptide (28-36), GLP-1 (7-36)amide, or GLP-1 metabolite (9-36) amide and a pharmaceutically acceptable carrier; and administering to graft recipient a second composition consisting of GLP-1 peptide (28-36), GLP-1 (7-36)amide, or GLP-1 metabolite (9-36) amide and a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by infusion (i.e., intravenous drip), subcutaneous, intraperitoneal, transdermally, or intramuscular injection. The pharmaceutical composition may also be delivered via direct perfusion or bathing of a donor organ, tissue, or cell. It is also contemplated herein, that multiple routes of administration can be advantageous employing one route for the donor subject or organ and one or more routes of administration for a recipient. Thus, disclosed herein are methods of preventing, reducing, or inhibiting, DGF, allograft rejection or ischemic/reperfusion injury comprising contacting a donor organ tissue or cell with a composition comprising GLP-1 (7-36)amide, GLP-1 (9-36)amide, or GLP-1 (28-36); and administering to a graft recipient a composition comprising GLP-1 (7-36)amide, GLP-1 (9-36) amide, or GLP-1 (28-36), wherein the composition is administered to the recipient through continuous infusion. Also disclosed are methods of preventing, reducing, or inhibiting, DGF, allograft rejection or ischemic/reperfusion injury wherein the composition is administered to the donor graft via perfusion or bathing.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines Therapeutic Uses Although the typical dosages for the disclosed compositions and methods as used in the examples described herein was provided at a rate of 1.5 pmol/kg/min, it is understood that dosage and rate are affected by variables such route of administration and the subject receiving the composition. It is further understood that effective dosages and schedules for administering the compositions may be determined empirically, and making such determinations is within the skill in the art. The dosage ranges for the administration of the compositions are those large enough to produce the desired effect in which the symptoms of the disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products.

Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Disclosed herein are compositions for preventing/reducing/inhibiting DGF, allograft rejection, injury from stroke, or ischemic/reperfusion injury comprising GLP-1 peptide (28-36), GLP-1 metabolite (7-36)amide, or GLP-1 metabolite (9-36)amide and a pharmaceutical carrier. It is understood and herein contemplated that there can be occasions where additional aspects to a composition are or not desired. Thus, for example, disclosed herein are compositions for preventing/reducing/inhibiting DGF, allograft rejection, injury from stroke, or ischemic/reperfusion injury consisting of GLP-1 peptide (28-36), GLP-1 metabolite (7-36)amide, or GLP-1 metabolite (9-36)amide and a pharmaceutical carrier. Additionally, disclosed herein are GLP-1 compositions comprising additional agents such as cryo-preservative solutions for donor organ preservation such as Wisconsin solution. Thus, for example disclosed herein are compositions comprising Wisconsin solution and GLP-1 peptide (28-36), GLP-1 metabolite (7-36)amide, or GLP-1 metabolite (9-36)amide.

Peptides
Protein Variants

In addition, to the known functional GLP-1 strain variants, there are derivatives of the GLP-1 proteins which also function in the disclosed methods and compositions. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 1 and 2 and are referred to as conservative substitutions.

TABLE 1

Amino Acid Abbreviations

| Amino Acid | Abbreviations | |
|---|---|---|
| Alanine | Ala | A |
| allosoleucine | AIle | |
| Arginine | Arg | R |
| asparagine | Asn | N |
| aspartic acid | Asp | D |
| Cysteine | Cys | C |
| glutamic acid | Glu | E |
| Glutamine | Gln | Q |
| Glycine | Gly | G |
| Histidine | His | H |
| Isolelucine | Ile | I |
| Leucine | Leu | L |
| Lysine | Lys | K |
| phenylalanine | Phe | F |
| proline | Pro | P |
| pyroglutamic acid | pGlu | |
| Serine | Ser | S |
| Threonine | Thr | T |
| Tyrosine | Tyr | Y |
| Tryptophan | Trp | W |
| Valine | Val | V |

TABLE 2

Amino Acid Substitutions
Original Residue Exemplary Conservative
Substitutions, others are known in the art.

| | |
|---|---|
| Ala | Ser |
| Arg | Lys; Gln |
| Asn | Gln; His |
| Asp | Glu |
| Cys | Ser |
| Gln | Asn, Lys |
| Glu | Asp |
| Gly | Pro |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, are accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T.E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. For example, SEQ ID NO: 1 sets forth a particular sequence of GLP-1 (7-36); SEQ ID NO:2 sets forth a particular sequence of GLP-1 (9-36) amide; and SEQ ID NO: 3 sets forth a particular sequence of GLP-1 (28-36). Specifically disclosed are variants of these and other proteins herein disclosed which have at least 70% homology to the stated sequence. Also disclosed are variants of these and other proteins herein disclosed which have at least 75% homology to the stated sequence. Also disclosed are variants of these and other proteins herein disclosed which have at least 80% homology to the stated sequence. Also disclosed are variants of these and other proteins herein disclosed which have at least 85% homology to the stated sequence. Also disclosed are variants of these and other proteins herein disclosed which have at least 90% homology to the stated sequence. Also disclosed are variants of these and other proteins herein disclosed which have at least 95% homology to the stated sequence. Also disclosed are variants of these and other proteins herein disclosed which have at least 97% homology to the stated sequence. Also disclosed are variants of these and other proteins herein disclosed which have at least 98% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. For example, one of the many nucleic acid sequences that can encode the protein sequence set forth in SEQ ID NO:1 is set forth in SEQ ID NO:4 (CACGCGGAGGGTACGTTTACTTCA-GATGTGTCCAGCTATCTTGAGGG TCAGGCA-GCTAAGGAATTTATAGCGTGGCTTGTGAAGGGC-CGA). In addition, for example, a disclosed conservative derivative of SEQ ID NO:1 is shown in SEQ ID NO: 7 (HAEGTFTSDVSSYLEGQAAKEFVAWLVKGR), where the isoleucine (I) at position 29 is changed to a valine (V). It is also understood that while no amino acid sequence indicates what particular DNA sequence encodes that protein within an organism, where particular variants of a disclosed protein are disclosed herein, the nucleic acid sequence that encodes that protein is also herein disclosed and described.

It is understood that there are numerous amino acid and peptide analogs which can be incorporated into the disclosed compositions. For example, there are numerous D amino acids or amino acids which have a different functional substituent then the amino acids shown in Table 1 and Table 2. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., *Methods in Molec. Biol.* 77:43-73 (1991), Zoller, Current Opinion in *Biotechnology*, 3:348-354 (1992); Ibba, *Biotechnology & Genetic Enginerring Reviews* 13:197-216 (1995), Cahill et al., *TIBS,* 14(10):400-403 (1989); Benner, *TIB Tech,* 12:158-163 (1994); Ibba and Hennecke, *Bio/technology,* 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—, —CH═CH— (cis and trans), —$COCH_2$—, —CH(OH) $CH_2$—, and —$CHH_2SO$— (These and others can be found in Spatola, A. F. in *Chemistry and Biochemistry of Amino Acids, Peptides, and Proteins*, B. Weinstein, eds., Marcel Dekker, New York, p. 267 (1983); Spatola, A. F., *Vega Data* (March 1983), Vol. 1, Issue 3, Peptide Backbone Modifications (general review); Morley, *Trends Pharm Sci* (1980) pp. 463-468; Hudson, D. et al., Int J Pept Prot Res 14:177-185 (1979) (—$CH_2NH$—, $CH_2CH_2$—); Spatola et al. *Life Sci* 38:1243-1249 (1986) (—CH $H_2$—S); Hann *J. Chem. Soc Perkin Trans*. I 307-314 (1982) (—CH—CH—, cis and trans); Almquist et al. J. Med. Chem. 23:1392-1398 (1980) (—$COCH_2$—); Jennings-White et al. *Tetrahedron Lett* 23:2533 (1982) (—$COCH_2$—); Szelke et al. European Appln, EP 45665 CA (1982): 97:39405 (1982) (—CH(OH) $CH_2$—); Holladay et al. *Tetrahedron. Lett* 24:4401-4404 (1983) (—C(OH)$CH_2$—); and Hruby *Life Sci* 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

Nucleic Acids

There are a variety of molecules disclosed herein that are nucleic acid based, including for example the nucleic acids that encode, for example GLP-1 (7-3), GLP-1 (9-36)amide, OR GLP-1 (28-36), or fragments thereof, as well as various functional nucleic acids. The disclosed nucleic acids are made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenine-9-yl (A), cytosine-1-yl (C), guanine-9-yl (G), uracil-1-yl (U), and thymin-1-yl (T). The sugar moiety of a nucleotide is a ribose or a deoxyribose. The phosphate moiety of a nucleotide is pentavalent phosphate. A non-limiting example of a nucleotide would be 3'-AMP (3'-adenosine monophosphate) or 5'-GMP (5'-guanosine monophosphate). There are many varieties of these types of molecules available in the art and available herein.

A nucleotide analog is a nucleotide which contains some type of modification to either the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties. There are many varieties of these types of molecules available in the art and available herein.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid. There are many varieties of these types of molecules available in the art and available herein.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety. (Letsinger et al., *Proc. Natl. Acad. Sci. USA,* 1989, 86, 6553-6556). There are many varieties of these types of molecules available in the art and available herein.

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

Sequence Similarities

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have between 70 to 100 percent homology, 80-100 percent homology, 90 to 100 percent homology, 95 to 100 percent homology, or 98 to 100 percent homology to the stated sequence or the native sequence. Thus, for example, variant of genes and proteins herein disclosed have at least 70 percent homology to the stated sequence or native sequence. Also, for example, variant of genes and proteins herein disclosed have at least 75 percent homology to the stated sequence or native sequence. Alternatively, for example, variant of genes and proteins herein disclosed have at least 80 percent homology to the stated sequence or native sequence. In another aspect, for example, variant of genes and proteins herein disclosed have at least 85 percent homology to the stated sequence or native sequence. In another aspect, for example, variant of genes and proteins herein disclosed have at least 90 percent homology to the stated sequence or native sequence. Also, for example, variant of genes and proteins herein disclosed have at least 95 percent homology to the stated sequence or native sequence. Alternatively, for example, variant of genes and proteins herein disclosed have at least 98 percent homology to the stated sequence or native sequence. Thus, for example, variant of genes and proteins herein disclosed have at least 100 percent homology to the stated sequence or native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman *Adv. Appl. Math.* 2: 482 (1981), by the homology alignment algorithm of Needleman and Wunsch, *J. Mol. Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

Delivery of the Compositions to Cells

It is understood and herein contemplated that the method by which the compositions are delivered to the graft, the graft recipient, or subject suffering from an ischemic/reperfusion injury, depends on the form in which theGLP-1 composition is administered. Where GLP-1 (7-36)amide, GLP-1 (9-36)amide, or GLP-1 (28-36) is administered as a peptide either in a diluent alone or part of a larger composition, the route of administration is via injection, infusion, or perfusion.

However, it is understood that for long term administration (i.e., greater than 72 hours), continuous infusion may not be desirable or possible. In situations where continuous infusion would be needed but not provided, administration of GLP-1 (7-36)amide, GLP-1 (9-36)amide, or GLP-1 (28-36) can be accomplished through expression of the nucleic acid encoding GLP-1 (7-36)amide, GLP-1 (9-36)amide, or GLP-1 (28-36) in a cell.

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., *Science*, 247, 1465-1468, (1990); and Wolff, J. A. *Nature*, 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier. Therefore, disclosed herein are methods of for preventing/reducing/inhibiting DGF, allograft rejection, injury from stroke, or ischemic/reperfusion injury, wherein the GLP-1 composition is administered to the recipient or subject having suffered ischemic/reperfusion injury or injury due to stroke as a nucleic acid which encodes GLP-1 and which nucleic acid is, for example, encoded on a vector such as a viral vector or plasmid. For example, also disclosed are viral vectors comprising a nucleic acid that encodes GLP-1 peptide (28-36), GLP-1 (7-36)amide, or GLP-1 metabolite (9-36)amide operably linked to a promoter.

Nucleic Acid Based Delivery Systems

Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)).

As used herein, plasmid or viral vectors are agents that transport the disclosed nucleic acids, such as GLP-1 (7-3) amide, GLP-1 (9-36)amide, OR GLP-1 (28-36) into the cell without degradation and include a promoter yielding expression of the gene in the cells into which it is delivered. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transaction (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

Retroviral Vectors

A retrovirus is an animal virus belonging to the virus family of Retroviridae, including any types, subfamilies, genus, or tropisms. Retroviral vectors, in general, are described by Verma, I. M., Retroviral vectors for gene transfer. In Microbiology-1985, American Society for Microbiology, pp. 229-232, Washington, (1985), which is incorporated by reference herein. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

Adenoviral Vectors

The construction of replication-defective adenoviruses has been described (Berkner et al., *J. Virology* 61:1213-1220 (1987); Massie et al., *Mol. Cell. Biol.* 6:2872-2883 (1986); Haj-Ahmad et al., *J. Virology* 57:267-274 (1986); Davidson et al., *J. Virology* 61:1226-1239 (1987); Zhang "Generation and identification of recombinant adenovirus by liposome-mediated transfection and PCR analysis" *BioTechniques* 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, *J. Clin. Invest.* 92:1580-1586 (1993); Kirshenbaum, *J. Clin. Invest.* 92:381-387 (1993); Roessler, *J. Clin. Invest.* 92:1085-1092 (1993); Moullier, *Nature Genetics* 4:154-159 (1993); La Salle, *Science* 259:988-990 (1993); Gomez-Foix, *J. Biol. Chem.* 267:25129-25134 (1992); Rich, Human Gene Therapy 4:461-476 (1993); Zabner, *Nature Genetics* 6:75-83 (1994); Guzman, *Circulation Research* 73:1201-1207 (1993); Bout, *Human Gene Therapy* 5:3-10 (1994); Zabner, *Cell* 75:207-216 (1993); Caillaud, *Eur. J. Neuroscience* 5:1287-1291 (1993); and Ragot, *J. Gen. Virology* 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, *Virology* 40:462-477 (1970); Brown and Burlingham, *J. Virology* 12:386-396 (1973); Svensson and Persson, *J. Virology* 55:442-449 (1985); Seth, et al., *J. Virol.* 51:650-655 (1984); Seth, et al., *Mol. Cell. Biol.* 4:1528-1533 (1984); Varga et al., *J. Virology* 65:6061-6070 (1991); Wickham et al., *Cell* 73:309-319 (1993)).

A viral vector can be one based on an adenovirus which has had the E1 gene removed and these virons are generated in a cell line such as the human 293 cell line. In another preferred embodiment both the E1 and E3 genes are removed from the adenovirus genome.

Adeno-Asscociated Viral Vectors

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV LTRs, or modifications thereof, confer infectivity and site-specific integration, but not cytotoxicity, and the promoter directs cell-specific expression. U.S. Pat. No. 6,261,834 is herein incorporated by reference for material related to the AAV vector.

The disclosed vectors thus provide DNA molecules which are capable of integration into a mammalian chromosome without substantial toxicity.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

Large Payload Viral Vectors

Molecular genetic experiments with large human herpesviruses have provided a means whereby large heterologous DNA fragments can be cloned, propagated and established in cells permissive for infection with herpesviruses (Sun et al., *Nature genetics* 8: 33-41, 1994; Cotter and Robertson,. *Curr Opin Mol Ther* 5: 633-644, 1999). These large DNA viruses (herpes simplex virus (HSV) and Epstein-Barr virus (EBV), have the potential to deliver fragments of human heterologous DNA >150 kb to specific cells. EBV recombinants can maintain large pieces of DNA in the infected B-cells as episomal DNA. Individual clones carried human genomic inserts up to 330 kb appeared genetically stable. The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA >220 kb and to infect cells that can stably maintain DNA as episomes.

Other useful systems include, for example, replicating and host-restricted non-replicating vaccinia virus vectors.

Non-Nucleic Acid Based Systems

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed GLP-1 (7-3)amide, GLP-1 (9-36)amide, OR GLP-1 (28-36) or vectors for example, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. *Am. J. Resp. Cell. Mol. Biol.* 1:95-100 (1989); Felgner et al. *Proc. Natl. Acad. Sci. USA* 84:7413-7417 (1987); U.S. Pat. No. 4,897, 355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., Bioconjugate Chem., 2:447-451, (1991); Bagshawe, K. D., Br. J. Cancer, 60:275-281, (1989); Bagshawe, et al., Br. J. Cancer, 58:700-703, (1988); Senter, et al., Bioconjugate Chem., 4:3-9, (1993); Battelli, et al., Cancer Immunol. Immunother., 35:421-425, (1992); Pietersz and McKenzie, Immunolog. Reviews, 129:57-80, (1992); and Roffler, et al., Biochem. Pharmacol, 42:2062-2065, (1991)). These techniques can be used for a variety of other specific cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., Cancer Research, 49:6214-6220, (1989); and Litzinger and Huang, Biochimica et Biophysica Acta, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

Nucleic acids that are delivered to cells which are to be integrated into the host cell genome, typically contain integration sequences. These sequences are often viral related sequences, particularly when viral based systems are used. These viral integration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

In Vivo/Ex Vivo

As described above, the compositions can be administered in a pharmaceutically acceptable carrier and can be delivered to the subject's cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

Viral Promoters and Enhancers

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., Nature, 273: 113 (1978)). The immediate early promoter of the human cytomegalovirus is conveniently obtained as a HindIII E restriction fragment (Greenway, P. J. et al., Gene 18: 355-360 (1982)). Of course, promoters from the host cell or related species also are useful herein.

Enhancer generally refers to a sequence of DNA that functions at no fixed distance from the transcription start site and can be either 5' (Laimins, L. et al., Proc. Natl. Acad. Sci. 78: 993 (1981)) or 3' (Lusky, M. L., et al., Mol. Cell. Bio. 3: 1108 (1983)) to the transcription unit. Furthermore, enhancers can be within an intron (Banerji, J. L. et al., Cell 33: 729 (1983)) as well as within the coding sequence itself (Osborne, T. F., et al., Mol. Cell. Bio. 4: 1293 (1984)). They are usually between 10 and 300 by in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, -fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

Markers

The viral vectors can include nucleic acid sequence encoding a marker product. This marker product is used to determine if the gene has been delivered to the cell and once delivered is being expressed. Preferred marker genes are the *E. Coli* lacZ gene, which encodes β-galactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., J. Molec. Appl. Genet. 1: 327 (1982)), mycophenolic acid, (Mulligan, R. C. and Berg, P. Science 209: 1422 (1980)) or hygromycin, (Sugden, B. et al., Mol. Cell. Biol. 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

Methods of Making the Compositions

The compositions disclosed herein and the compositions necessary to perform the disclosed methods can be made using any method known to those of skill in the art for that particular reagent or compound unless otherwise specifically noted.

Nucleic Acid Synthesis

For example, the nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook et al., Molecular Cloning: A Laboratory Manual, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., Ann. Rev. Biochem. 53:323-356 (1984), (phosphotriester and phosphite-triester methods), and Narang et al., Methods Enzymol., 65:610-620 (1980), (phosphotriester method). Protein nucleic acid molecules can be made using known methods such as those described by Nielsen et al., Bioconjug. Chem. 5:3-7 (1994).

Peptide Synthesis

One method of producing the disclosed proteins, such as SEQ ID NOs: 1, 2, or 3, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof (Grant GA (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

GLP-1 (7-36) Amide Improves Recovery Following Ischemic Injury when Administered at the Time of Reperfusion Extensive studies from our laboratory have documented that GLP-1 mitigates ischemic injury in both relevant large animal models and in humans. FIG. 1 demonstrates that GLP-1 (7-36) amide administered at the time of reperfusion following coronary artery occlusion at a dose of 1.5 pmol/kg/min leads to more rapid and complete recovery of left ventricular function in conscious dogs. This mechanism involves improved ventricular relaxation which is known to be most sensitive to ATP depletion. FIG. 2 illustrates that GLP-1 (7-36) amide at a dose of 1.5 pmol/kg/min administered at the time of reperfusion in humans with acute myocardial infarction is associated with improved peri-infarct and global LV function compared to patients treated with comparable therapies but without GLP-1. It has been shown that GLP-1 infusion reduces the requirement for inotropic and pressure support.

Example 2

GLP-1 Improves Renal Blood Flow and Function and Causes a Natriuresis

Figures 4, 4A:
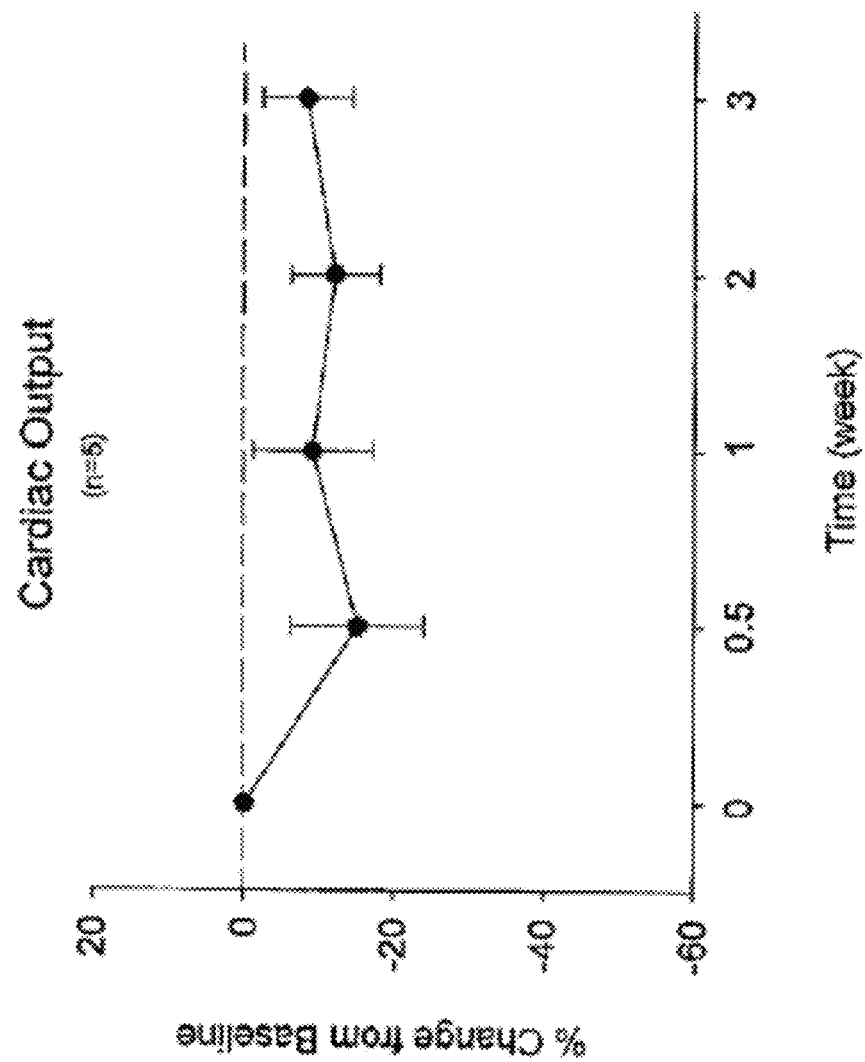
FIG. 4, comprising
FIG. 4A and 4B show impaired renal blood flow but not cardiac output in pigs with biventricular failure.
Figures 4, 4B:
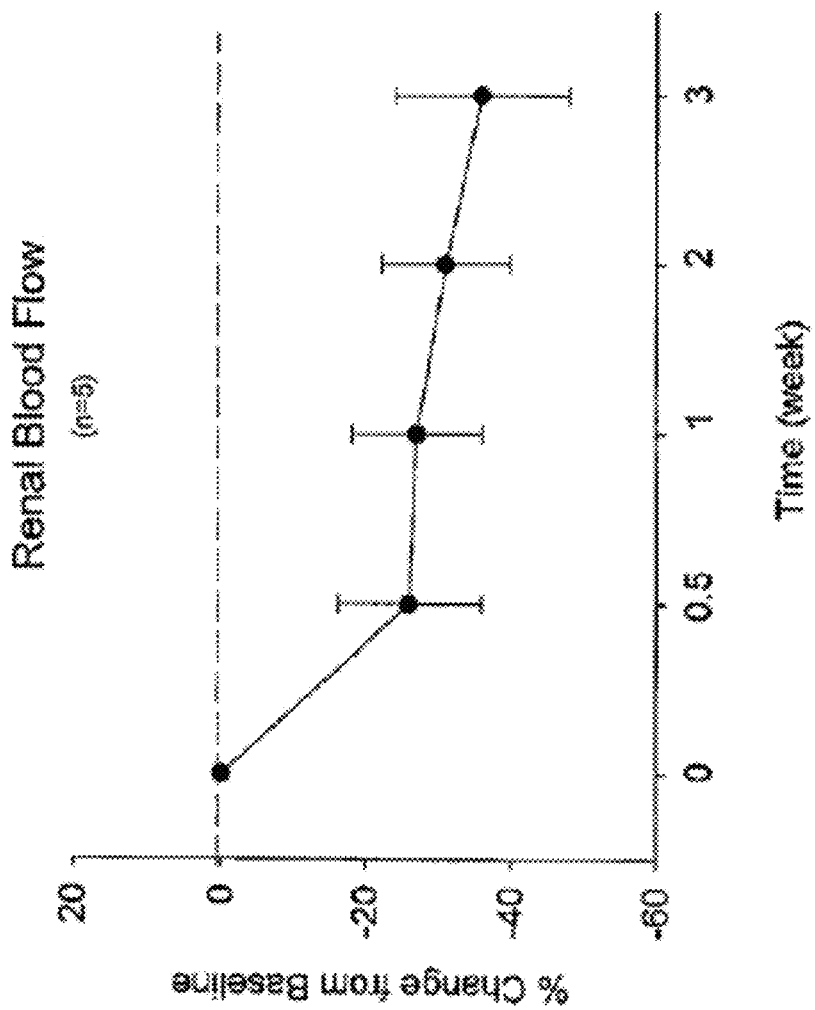
Figure 5:
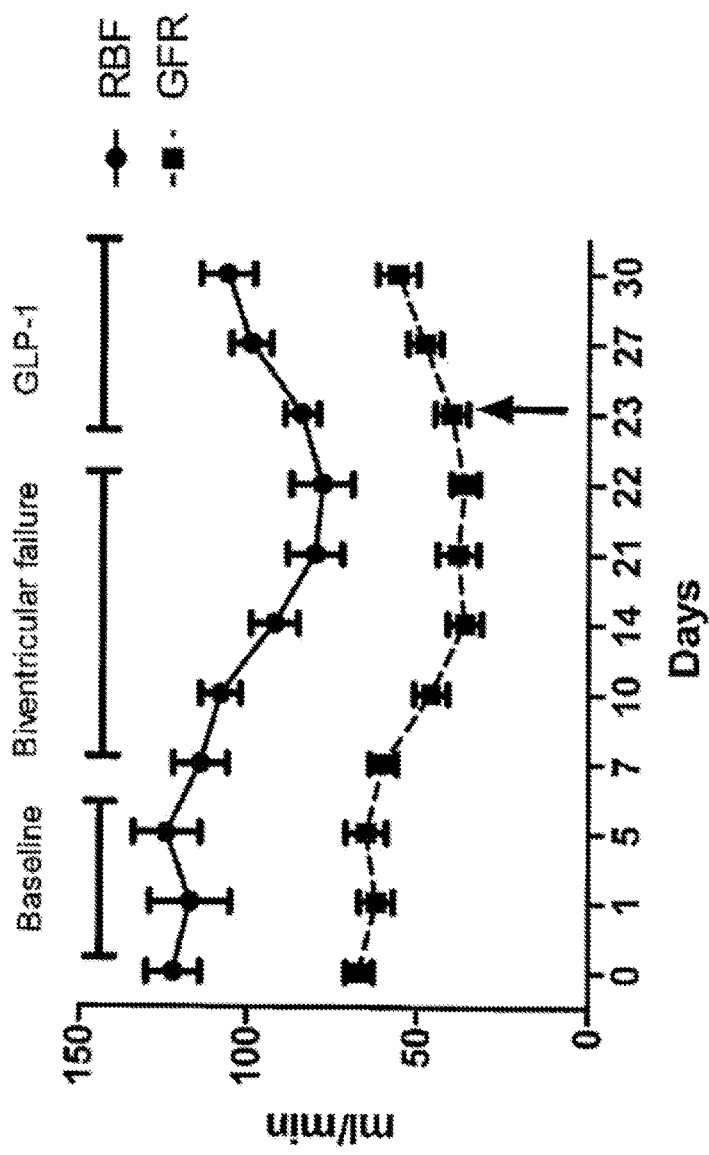
FIG. 5 shows the favorable effects of GLP-1 on renal blood flow and Glomerular Filtration Rate

There is a model of biventricular heart failure in conscious pigs that is associated with reductions in renal blood flow and function. FIG. 3 illustrates the model and the perturbation in renal blood flow. This is an important model of cardio-renal syndrome in which renal and cardiac injury are found together. FIG. 4 illustrates a 50% reduction in renal blood flow without a reduction in cardiac output in conscious pigs with biventricular failure. FIG. 5 illustrates the effects of a short term (2 hours) GLP-1 infusion (1.5 pmol/kg/min) on renal blood flow and sodium excretion in conscious pigs with biventricular failure. GLP-1 returned renal blood flow to near normal levels and is associated with increased urinary sodium excretion and improvement in GFR. FIG. 6 illustrates that GLP-1 (7-36) amide administered to patients with Class 3-4 heart failure for 5 weeks is associated with a significant natriuresis that required reduction in diuretic doses.

Example 3

The Cellular Mechanism by which GLP-1 Improves Recovery from Ischemic Injury.

Figure 7:
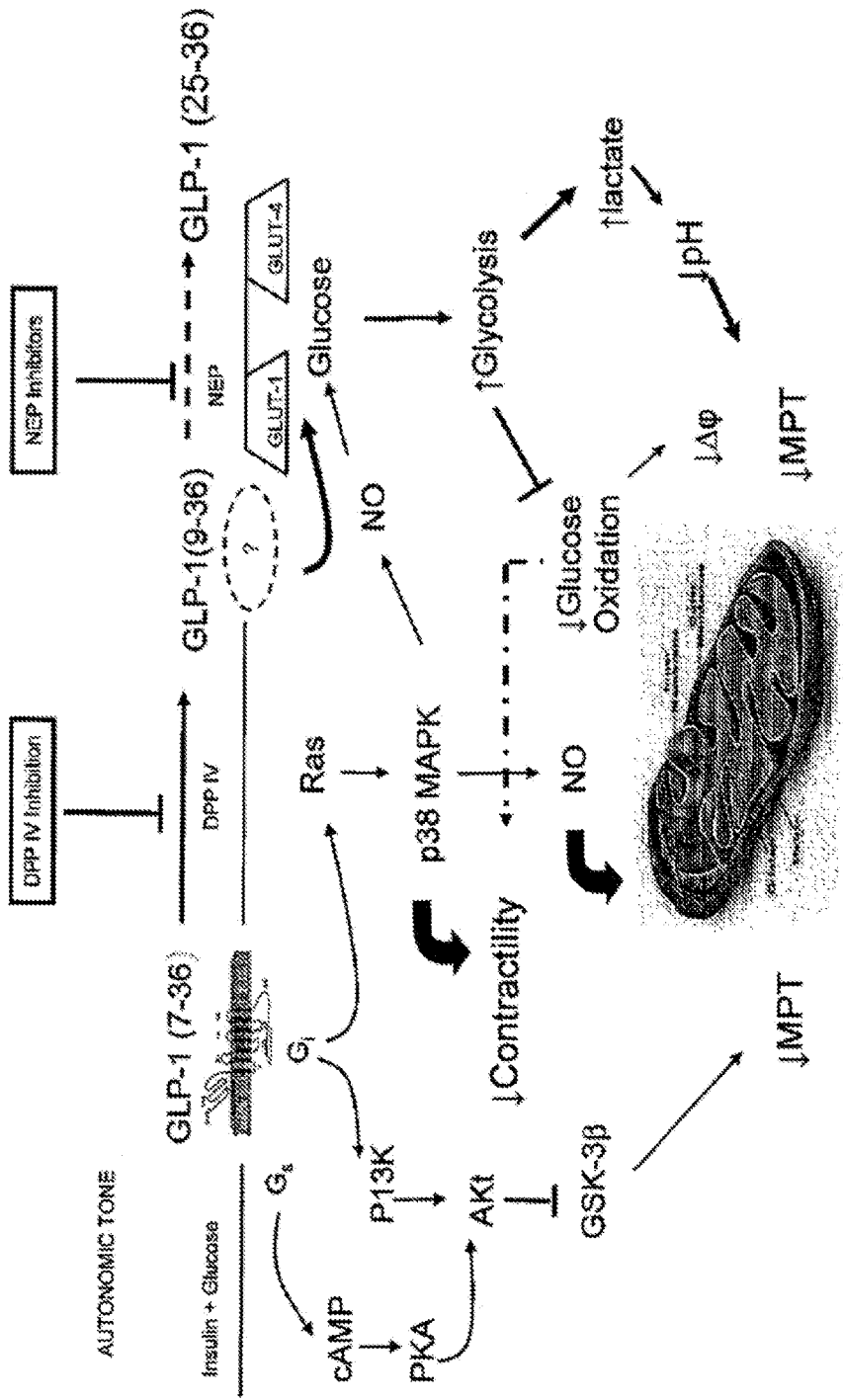
FIG. 7 shows the proposed GLP-1 Signaling Pathway in Normal Myocardium.
Figure 8:
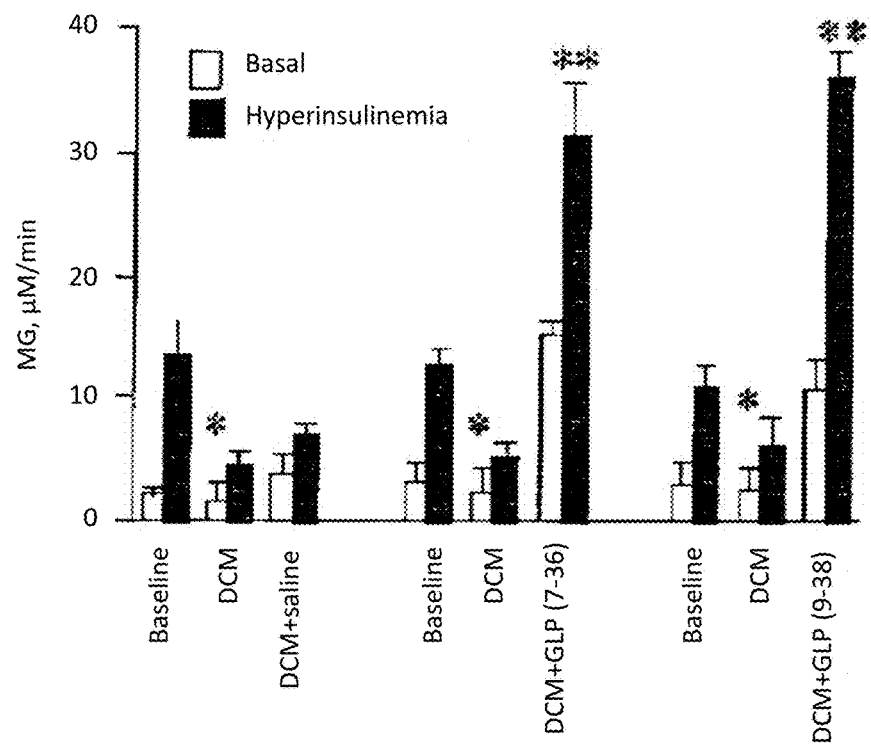
FIG. 8 shows that both GLP-1 7-36 amide and GLP-1 9-36 amide increase myocardial glucose uptake. The Effects of GLP-1 (7-36)amide (n=5 dogs) or GLP-1 (9-36amide (n=5 dogs) on basal (preclamp) and insulin-stimulated myocardial glucose (MG) uptake (A) and CBF (B) during hyperinulinemic euglycemic clamp in conscious dogs with pacing-induced DCM. *$P<0.05$ compared with response in saline control (n=5 dogs); **$P<0.05$ compared with response in DCM.
Figures 8, 8B:
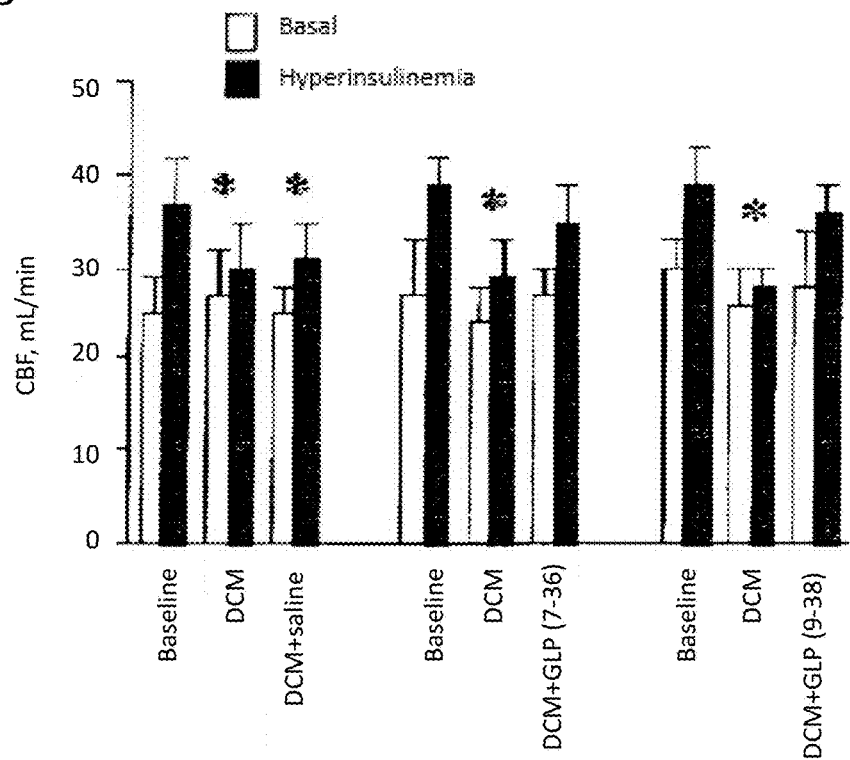

There are two mechanisms that have been established whereby GLP-1 (7-36) amide improves recovery following ischemic injury (FIG. 7). Firstly, GLP-1 increases target organ glucose uptake without the requirement for exogenous insulin. This provides glycolytic ATP without further increases in mitochondrial ROS production. Secondly, GLP-1 induces a cellular signaling program involving p38 MAP kinase which increases NOS2 and mitigates ROS production. The combined cellular signaling mechanisms involve actions through the GLP-1 receptor and through the metabolite (GLP-1 9-36) amide. This provides the rationale for the use of the native peptide in the treatment of post-ischemic allograft injury. Both GLP-1 (7-36) amide and GLP-1 (9-36) amide have been shown to increase myocardial glucose uptake independent of an increase in circulating insulin as shown in FIG. 8.

Figure 9:
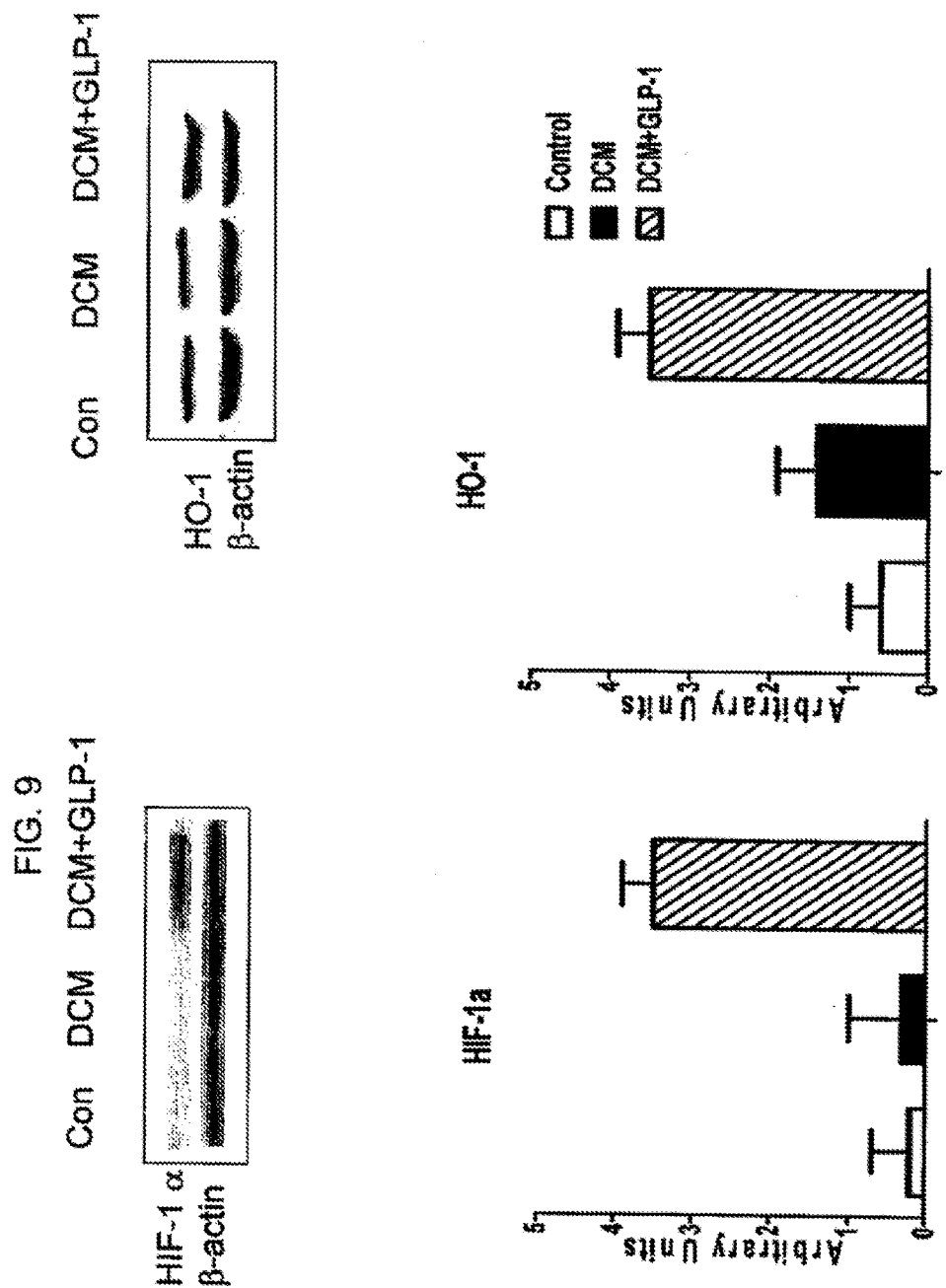
FIG. 9 shows evidence to suggest that GLP-1 induces HIF-1a as an organ protective mechanism prior to ischemia.

FIG. 9 illustrates evidence to suggest that GLP-1 induces HIF-1a as an organ protective mechanism prior to ischemia through a p38 MAP kinase dependent mechanism. In normal hearts, GLP-1 treatment via intravenous continuous administration results in an increases in HIF-1a mRNA and increased expression of HIF-1a inducible genes, heme-oxygenase-1 (HO-1). The induction of this cyto-protective program is beneficial in the face of subsequent ischemic injury in allografts. p38 MAP kinase activation has been associated with the stabilization of praline residues which otherwise target the HIF-1a subunits to ubiquinization. The stabilization allows the subunits to form heterodimers which active a gene program of cytoprotection.

Example 4

Synthesis and Purification of GLP-1 (7-36) Amide for Clinical Studies

The solid-phase peptide synthesis is performed on a Applied Biosystems model 431A synthesizer using 9-Fluoenlmethoxycarbony (Fmoc) chemistry. The polypeptide chain is assembled by successive incorporations of the derivatized amino acids using DCC/HOBt (dicylohexylcarbodiimide (DCC), 1-hydroxybenzotriazole (HOBt)) activation and extended single couplings. The polypeptide is then cleaved from resin and deprotected in a single step. The peptide is then precipitated by filtering the cleavage mixture directly into cold MTBE (methyl tert-butyl ether (MTBE)). The precipitate is washed three times with MTBE, in order to remove salts. The precipitate is then solubilized in 20% acetonitrile in water and lyophilized.

The crude peptide is purified in two steps on C-18 reversed-phase columns using Waters preparative scale (Delta-Prep) system equipped with Delta-Pack column. The first step of chromatography consists of two separate runs on a Vydac preparative column. The column is eluted with a gradient consisting of H2O/).1% trifluoroacetic acid and acetonitrile/0.1% TFA. This partially purified peptide (85% pure) is further purified by reloading on the same column.

The homogeneity of the final purified peptide is greater than 99% by HPLV analysis. Mass units was determined by Matrix Assisted Laser Desorption/Ionization Time of Flight MALDI-TOF) Mass Spectrometry. The obtained value corresponds to the calculated molecular weight of the full length of GLP-1 (7-36) amide. Acid hydrolysis of the final product followed by amino acid analysis showed the presence of all amino acids with the exception of Tryptophan. A net content of 88.84% was calculated from the data.

Sequences

Amino Acid Sequence for GLP-1(7-36)amide
SEQ ID NO: 1
HAEGTFTSDVSSYLEGQAAKEFIAWLVKGR Amino Acid Sequence for GLP-1(9-36)amide
SEQ ID NO: 2
EGTFTSDVSSYLEGQAAKEFIAWLVKGR Amino Acid Sequence for GLP-1(28-36)
SEQ ID NO: 3
FIAWLVKGR Nucleic Acid Sequence for GLP-1(7-36)amide
SEQ ID NO: 4
CACGCGGAGGGTACGTTTACTTCAGATGTGTCCAGCTATCTTGAGGGT

CAGGCAGCTAAGGAATTTATAGCGTGGCTTGTGAAGGGCCGA

Nucleic Acid Sequence for GLP-1(9-36)amide
SEQ ID NO: 5
GAGGGTACGTTTACTTCAGATGTGTCCAGCTATCTTGAGGGTCAGGCA

GCTAAGGAATTTATAGCGTGGCTTGTGAAGGGCCGA

Nucleic Acid Sequence for GLP-1(28-36)
SEQ ID NO: 6
TTTATAGCGTGGCTTGTGAAGGGCCGA

Amino Acid Sequence for GLP-1(7-36)amide variant
SEQ ID NO: 7
HAEGTFTSDVSSYLEGQAAKEFVAWLVKGR

What is claimed:

1. A composition for treating or reducing delayed graft function (DGF), allograft rejection, or ischemic or reperfusion injury, said composition comprising a therapeutically effective amount of: Wisconsin solution, GLP-1 peptide (28-36), and GLP-1 metabolite (9-36)amide.

2. A composition for treating or reducing delayed graft function (DGF), allograft rejection, or ischemic or reperfusion injury, said composition consisting essentially of a therapeutically effective amount of a pharmaceutical carrier, GLP-1 peptide (28-36), and GLP-1 metabolite (9-36)amide.

3. A composition for treating or reducing delayed graft function (DGF), allograft rejection, or ischemic or reperfusion injury, said composition consisting essentially of a therapeutically effective amount of a pharmaceutical carrier and GLP-1 peptide (28-36).

4. A composition for treating or reducing delayed graft function (DGF), allograft rejection, or ischemic or reperfusion injury, said composition comprising a therapeutically effective amount of a pharmaceutical carrier and GLP-1 peptide (28-36).

5. A method of treating or reducing delayed graft function (DGF), allograft rejection, or ischemia/reperfusion injury, comprising:
   a) contacting a donor organ, tissue, or cell graft with a first composition wherein the first composition is selected from the group consisting of: i) a composition comprising a therapeutically effective amount of: Wisconsin solution, GLP-1 peptide (28-36), and GLP-1 metabolite (9-36)amide; ii) a composition consisting essentially of a therapeutically effective amount of a pharmaceutical carrier, GLP-1 peptide (28-36), and GLP-1 metabolite (9-36)amide; iii) a composition consisting essentially of a therapeutically effective amount of a pharmaceutical carrier and GLP-1 peptide (28-36); and iv) a composition comprising a therapeutically effective amount of a pharmaceutical carrier and GLP-1 peptide (28-36); and
   b) administering to a graft recipient a second composition wherein the second composition is selected from the group consisting of: i) a composition comprising a therapeutically effective amount of: Wisconsin solution, GLP-1 peptide (28-36), and GLP-1 metabolite (9-36)amide; ii) a composition consisting essentially of a therapeutically effective amount of a pharmaceutical carrier, GLP-1 peptide (28-36), and GLP-1 metabolite (9-36)amide; iii) a composition consisting essentially of a therapeutically effective amount of a pharmaceutical carrier and GLP-1 peptide (28-36); and iv) a composition comprising a therapeutically effective amount of a pharmaceutical carrier and GLP-1 peptide (28-36).

6. The method of claim 5, wherein the first and second composition are the same.

7. The method of claim 5, wherein the graft is contacted with the first composition by administering the first composition to a donor subject via continuous infusion.

8. The method of claim 5, wherein the donor organ, tissue, or cell is from a cadaveric donor.

9. The method of claim 8, wherein the donor organ, tissue, or cell is contacted with the composition by ex vivo perfusion or bathing.

10. The method of claim 5, wherein the second composition is first administered to the graft recipient as a preconditioning administration at time of graft harvest.

11. The method of claim 5, wherein the second composition is administered to the recipient for at least 72 hours following graft.

12. The method of claim 5, wherein the second composition is administered to the recipient parenterally.

13. The method of claim 5, wherein the second composition is administered to the recipient via continuous infusion.

14. The method of claim 5, further comprising a third composition wherein the third composition is selected from the group consisting of: i) a composition comprising a therapeutically effective amount of: Wisconsin solution, GLP-1peptide (28-36), and GLP-1 metabolite (9-36)amide; ii) a composition consisting essentially of a therapeutically effective amount of a pharmaceutical carrier, GLP-1 peptide (28-36), and GLP-1 metabolite (9-36)amide; iii) a composition consisting essentially of a therapeutically effective amount of a pharmaceutical carrier and GLP-1 peptide (28-36); and iv) a composition comprising a therapeutically effective amount of a pharmaceutical carrier and GLP-1 peptide (28-36).

15. The method of claim 14, wherein the third composition is administered to the recipient parenterally.

16. A method of treating or reducing delayed graft function, allograft rejection, or ischemia/reperfusion injury comprising contacting a donor organ, tissue, or cell graft with a first composition wherein the first composition is selected from the group consisting of: i) a composition comprising a therapeutically effective amount of: Wisconsin solution, GLP-1 peptide (28-36), and GLP-1 metabolite (9-36)amide; ii) a composition consisting essentially of a therapeutically effective amount of a pharmaceutical carrier, GLP-1 peptide (28-36), and GLP-1 metabolite (9-36)amide; iii) a composition consisting essentially of a therapeutically effective amount of a pharmaceutical carrier and GLP-1 peptide (28-36); and iv) a composition comprising a therapeutically effective amount of a pharmaceutical carrier and GLP-1 peptide (28-36).

17. A method of treating or reducing allograft rejection, said method comprising: administering to a recipient of a graft a composition selected from the group consisting of: i) a composition comprising a therapeutically effective amount of: Wisconsin solution, GLP-1 peptide (28-36), and GLP-1 metabolite (9-36)amide; ii) a composition consisting essentially of a therapeutically effective amount of a pharmaceutical carrier, GLP-1 peptide (28-36), and GLP-1 metabolite (9-36)amide; iii) a composition consisting essentially of a therapeutically effective amount of a pharmaceutical carrier and GLP-1 peptide (28-36); and iv) a composition comprising a therapeutically effective amount of a pharmaceutical carrier and GLP-1 peptide (28-36).

18. The method of claim 17, wherein the allograft rejection is an acute allograft rejection.

19. A method of prolonging allograft survival, said method comprising:
   a) contacting a donor organ, tissue, or cell graft with a first composition wherein the first composition is selected from the group consisting of: i) a composition comprising a therapeutically effective amount of: Wisconsin solution, GLP-1 peptide (28-36), and GLP-1 metabolite (9-36)amide; ii) a composition consisting essentially of a therapeutically effective amount of a pharmaceutical carrier, GLP-1 peptide (28-36), and GLP-1 metabolite (9-36)amide; iii) a composition consisting essentially of a therapeutically effective amount of a pharmaceutical carrier and GLP-1 peptide (28-36); and iv) a composition comprising a therapeutically effective amount of a pharmaceutical carrier and GLP-1 peptide (28-36); and
   b) administering to graft recipient a second composition wherein the second composition is selected from the group consisting of: i) a composition comprising a therapeutically effective amount of: Wisconsin solution, GLP-1 peptide (28-36), and GLP-1 metabolite (9-36)amide; ii) a composition consisting essentially of a therapeutically effective amount of a pharmaceutical carrier, GLP-1 peptide (28-36), and GLP-1 metabolite (9-36)amide; iii) a composition consisting essentially of a therapeutically effective amount of a pharmaceutical carrier and GLP-1 peptide (28-36); and iv) a composition comprising a therapeutically effective amount of a pharmaceutical carrier and GLP-1 peptide (28-36).

* * * * *

SEQUENCE LISTING

```
<160> NUMBER OF SEQ ID NOS: 7

<210> SEQ ID NO 1
<211> LENGTH: 30
<212> TYPE: PRT
<213> ORGANISM: Artificial Sequence
<220> FEATURE:
<223> OTHER INFORMATION: Description of artificial sequence note =
      synthetic construct

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 2
<211> LENGTH: 28
<212> TYPE: PRT
<213> ORGANISM: Artificial Sequence
<220> FEATURE:
<223> OTHER INFORMATION: Description of artificial sequence note =
      synthetic construct

<400> SEQUENCE: 2

Glu Gly Thr Phe Thr Ser Asp Val Ser Ser Tyr Leu Glu Gly Gln Ala
1               5                   10                  15

Ala Lys Glu Phe Ile Ala Trp Leu Val Lys Gly Arg
            20                  25

<210> SEQ ID NO 3
<211> LENGTH: 9
<212> TYPE: PRT
<213> ORGANISM: Artificial Sequence
<220> FEATURE:
<223> OTHER INFORMATION: Description of artificial sequence note =
      synthetic construct
```

```
<400> SEQUENCE: 3

Phe Ile Ala Trp Leu Val Lys Gly Arg
1               5

<210> SEQ ID NO 4
<211> LENGTH: 90
<212> TYPE: DNA
<213> ORGANISM: Artificial Sequence
<220> FEATURE:
<223> OTHER INFORMATION: Description of artificial sequence note =
      synthetic construct

<400> SEQUENCE: 4
cacgcggagg gtacgtttac ttcagatgtg tccagctatc ttgagggtca ggcagctaag      60
gaatttatag cgtggcttgt gaagggccga                                       90

<210> SEQ ID NO 5
<211> LENGTH: 84
<212> TYPE: DNA
<213> ORGANISM: Artificial Sequence
<220> FEATURE:
<223> OTHER INFORMATION: Description of artificial sequence note =
      synthetic construct

<400> SEQUENCE: 5
gagggtacgt ttacttcaga tgtgtccagc tatcttgagg gtcaggcagc taaggaattt      60
atagcgtggc ttgtgaaggg ccga                                             84

<210> SEQ ID NO 6
<211> LENGTH: 27
<212> TYPE: DNA
<213> ORGANISM: Artificial Sequence
<220> FEATURE:
<223> OTHER INFORMATION: Description of artificial sequence note =
      synthetic construct

<400> SEQUENCE: 6
tttatagcgt ggcttgtgaa gggccga                                          27

<210> SEQ ID NO 7
<211> LENGTH: 30
<212> TYPE: PRT
<213> ORGANISM: Artificial Sequence
<220> FEATURE:
<223> OTHER INFORMATION: Description of artificial sequence note =
      synthetic construct

<400> SEQUENCE: 7

His Ala Glu Gly Thr Phe Thr Ser Asp Val Ser Ser Tyr Leu Glu Gly
1               5                   10                  15

Gln Ala Ala Lys Glu Phe Val Ala Trp Leu Val Lys Gly Arg
            20                  25                  30
```